United States Patent [19]

Campbell et al.

[11] Patent Number: 4,542,132

[45] Date of Patent: Sep. 17, 1985

[54] CARDIAC STIMULATING CYCLIC SULFONAMIDO SUBSTITUTED 4-PIPERIDINO-QUINAZOLINE DERIVATIVES, COMPOSITIONS, AND METHOD OF USE THEREFOR

[75] Inventors: Simon F. Campbell, Kingsdown; Albert A. Jaxa-Chamiec, Marlow; David A. Roberts, Woodnesborough, all of England

[73] Assignee: Pfizer Inc., New York, N.Y.

[21] Appl. No.: 636,197

[22] Filed: Jul. 31, 1984

[30] Foreign Application Priority Data

Aug. 3, 1983 [GB] United Kingdom ............. 8320958

[51] Int. Cl.$^4$ ................ A61K 31/54; A61K 31/445; A61K 31/505; C07D 417/14
[52] U.S. Cl. ................................. 514/222; 514/259; 544/3; 544/8; 544/284; 544/293
[58] Field of Search ............... 544/3, 8, 284, 293; 424/246, 251; 514/222, 259

[56] References Cited

U.S. PATENT DOCUMENTS

| | | | |
|---|---|---|---|
| 3,517,005 | 6/1970 | Cronin et al. | 260/256.4 |
| 4,188,390 | 2/1980 | Campbell | 424/251 |
| 4,289,772 | 9/1981 | Campbell et al. | 424/250 |
| 4,370,328 | 1/1983 | Campbell et al. | 424/250 |
| 4,489,075 | 12/1984 | Campbell et al. | 424/246 |

FOREIGN PATENT DOCUMENTS 0094766 11/1983 European Pat. Off. ............ 424/246

OTHER PUBLICATIONS

U.S. Ser. No. 489,271, Campbell et al.

*Primary Examiner*—Henry R. Jiles
*Assistant Examiner*—J. G. Mullins
*Attorney, Agent, or Firm*—Charles J. Knuth; Albert E. Frost; J. Trevor Lumb

[57] ABSTRACT

A series of novel 4-piperidino-6,7-dimethoxyquinazoline compounds, further substituted on the piperidino group, and the pharmaceutically-acceptable salts thereof, possess cardiac stimulating activity in mammals. They are useful in the curative or prophylactic treatment of cardiac conditions, in particular heart failure.

17 Claims, No Drawings

CARDIAC STIMULATING CYCLIC SULFONAMIDO SUBSTITUTED 4-PIPERIDINO-QUINAZOLINE DERIVATIVES, COMPOSITIONS, AND METHOD OF USE THEREFOR

BACKGROUND OF THE INVENTION

This invention relates to new chemical compounds, which are of value as new medicinal agents. More particularly, these new chemical compounds are phosphodiesterase inhibitors and cardiac stimulants of which a preferred class selectively increases the force of myocardial contraction without producing significant increases in heart rate. The compounds are useful in the curative or prophylactic treatment of cardiac conditions, in particular heart failure.

Published European Patent Application No. 0094766 and U.S. Pat. No. 4,489,075 provide inter alia novel cardiac-stimulating quinazoline compounds of the formula

[Structure (I): 6,7-dimethoxyquinazoline with 4-piperidino group substituted with X–Y]

and their pharmaceutically acceptable salts;
wherein X is an alkylene group of the formula $$-\underset{\underset{\text{}}{}}{C}H CH_2-,$$
with R substituent where R is H, CH$_3$ or C$_2$H$_5$;
and Y is a group of the formula:

[Structures showing sulfonamide cyclic groups with SO$_2$]

where R$^1$ is H or C$_1$–C$_4$ alkyl;
and R$^2$ and R$^3$ are each independently H or CH$_3$.

We have now discovered that derivatives of such compounds which contain a hydroxyl group attached either to the 3- or 4-carbon atom of the piperidine ring or to the carbon atom of X attached to the piperidine ring have particularly advantageous properties.

SUMMARY OF THE INVENTION

According to the present invention, there are provided compounds of the formula (I) in which X and Y are as defined previously, and either:

(i) the piperidine ring is further substituted with a hydroxy group in the 3- or 4-position, and, if it is substituted with a hydroxy group in the 3-position, it can be further substituted in the same position with a C$_1$–C$_4$ alkyl group; or (ii) the carbon atom of X attached to the piperidine ring is further substituted with a hydroxy group. Thus, either the piperidino group is substituted with a hydroxyl group in the 4-position or (optionally with a C$_1$–C$_4$ alkyl group) in the 3-position, or X is $$-\underset{\underset{OH}{|}}{C}R-CH_2-,$$

where R is H, CH$_3$ or C$_2$H$_5$.

Preferred groups for the substituent Y are:

[Three cyclic sulfonamide structures]

and preferred groups for X are $$-\underset{\underset{OH}{|}}{\overset{\overset{R}{|}}{C}}-CH_2-$$

wherein R is CH$_3$ or C$_2$H$_5$.

Especially valuable compounds of the invention are those in which X is $$-\underset{\underset{OH}{|}}{\overset{\overset{CH_3}{|}}{C}}-CH_2- \text{ and Y is }$$

[two sulfonamide cyclic structures]

i.e. 2-{2-hydroxy-2-[1-(6,7-dimethoxy-quinazolin-4-yl)-piperid-4-yl]prop-1-yl}isothiazolidine-1,1-dioxide and 2-{2-hydroxy-2-[1-(6,7-dimethoxy-quinazolin-4-yl)piperid-4-yl]prop-1-yl}-5-methyltetrahydro-1,2,6-thiadiazine-1,1-dioxide.

DETAILED DESCRIPTION OF THE INVENTION

The pharmaceutically acceptable salts of the compounds of the formula (I) are preferably acid addition salts formed from acids which form non-toxic acid addition salts containing pharmaceutically acceptable anions, such as the hydrochloride, hydrobromide, hydroiodide, sulphate or bisulphate, phosphate or acid phosphate, acetate, maleate, fumarate, lactate, tartrate, citrate, gluconate and p-toluenesulphonate salts. The hydrochloride salts are preferred.

The cardiac stimulant activity of the compounds of the formula (I) of this invention is shown by their effectiveness in one or more of the following tests: (a) increasing the force of contraction in the isolated, spontaneously beating, guinea pig double atria or kitten right and left atria preparations; (b) increasing myocardial contractility (left ventricular dp/dt max.) in the anaesthetised cat or dog with a left ventricular catheter; (c) increasing myocardial contractility in the conscious dog with an implanted left ventricular transducer (dp/dt max.) or an exteriorised carotid artery loop (systolic time intervals).

In test (a) the positive inotropic and chronotropic responses of the atria to the test compound are measured at several doses and compared with the responses elicited by isoprenaline. The comparison of the dose response curves obtained gives a measure of the force versus rate selectivity of the test compound.

In test (b) the positive inotropic action of the test compound following intravenous administration is measured in the anaesthetised cat or dog. The magnitude and duration of this action, and the selectivity for increase in force versus frequency of contraction of the test compound are obtained, as are its peripheral effects, e.g. the effect on the blood pressure.

In test (c) the positive inotropic action of the test compound following intravenous or oral administration to a conscious dog with an implanted left ventricular transducer (dp/dt max.) or an exteriorised carotid artery loop (systolic time intervals) is measured. The magnitude of the inotropic action, the selectivity for increase in force versus frequency of contraction, and the duration of action of the inotropic effect of the test compound are all obtained.

The compounds of the invention can be administered alone but will generally be administered in admixture with a pharmaceutical carrier selected with regard to the intended route of administration and standard pharmaceutical practice. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, oral dosages of the compounds of the invention should typically be from 10 mg to 1 g daily, taken in 2 to 4 divided doses per day, for an average adult patient (70 kg). Dosages for intravenous administration, typically by infusion, should typically be from 1 to 700 mg per day for a typical adult patient, for example in the treatment of acute heart failure. Thus for a typical adult patient, individual tablets or capsules will typically contain from 10 to 250 mg of active compound, in a suitable pharmaceutically acceptable vehicle or carrier.

Thus the present invention provides a pharmaceutical composition comprising a compound of the formula (I) as defined above or pharmaceutically acceptable acid addition salt thereof together with a pharmaceutically acceptable diluent or carrier. The weight ratio of active ingredient to pharmaceutically-acceptable carrier or diluent will normally be in the range from 4:1 to 1:40.

The invention also provides a method of stimulating the heart of a mammalian subject, including a human being, which comprises administering to said mammalian subject, a compound of the formula (I) or salt thereof as defined above, or a pharmaceutical composition as defined above, in an amount sufficient to stimulate the heart of said mammalian subject.

The compounds of the invention may be prepared by a number of routes:

Route A

This method for preparing many compounds of the invention is illustrated as follows:

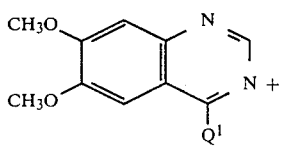

(II)

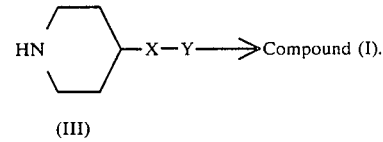

(III)

wherein X and Y are previously defined, either the piperidino ring or X in compound (III) being further substituted with a hydroxyl group, and the piperidino ring being optionally substituted with an alkyl group as well as a hydroxyl group in the 3-position, as previously described;

and $Q^1$ is an appropriate facile leaving group such as Cl, Br or I. $Q^1$ is preferably Cl.

The reaction is typically carried out in an organic solvent, e.g. ethanol, with heating at up to reflux temperature, for 2–15 hours. When $Q^1$ is Cl, Br or I, the presence of a non-nucleophilic base, e.g. a tertiary amine base such as triethylamine, is advantageous. The product can be isolated and purified by conventional procedures. An acid addition salt form of (III) can be used as the starting material although a base is preferably then present to neutralise the acid.

Starting materials of the formula (III) in which X is substituted with a hydroxyl group are either known compounds or can be prepared by conventional procedures, typically by the hydrogenation of the corresponding pyridines using hydrogen/$PtO_2$ under acidic conditions at 50°–60° C. and 50–60 p.s.i. until hydrogen uptake ceases, e.g. after 4–8 hours, or by N-debenzylation of the corresponding N-benzyl piperidine derivatives, using conventional procedures.

Typical routes to the pyridines, many of which are illustrated in detail in the following Preparations, are as follows:

(a)
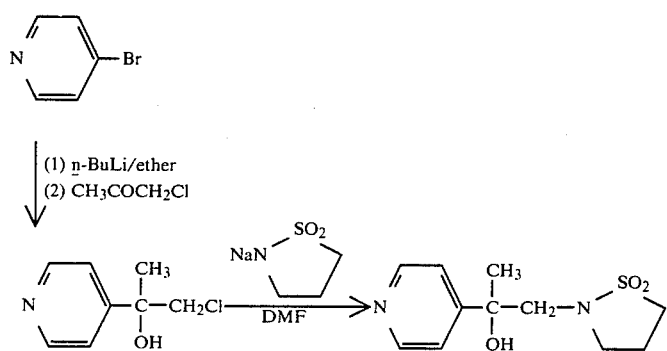
(b)
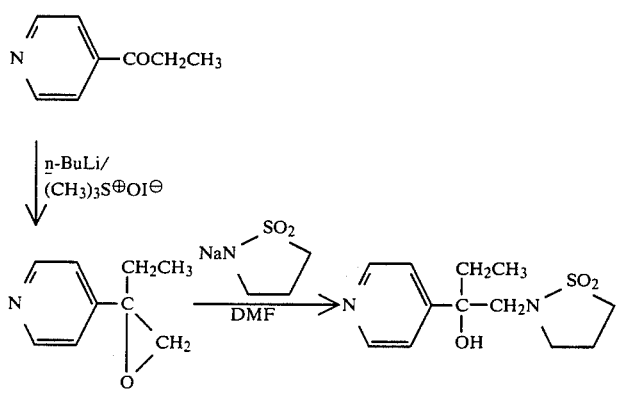
(c)
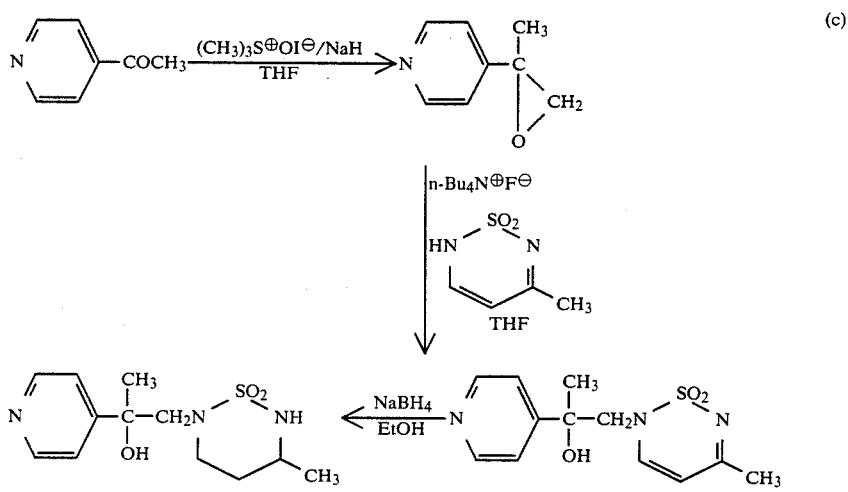
The N-benzylpiperidines may be prepared by similar routes, e.g. as follows:
(d)
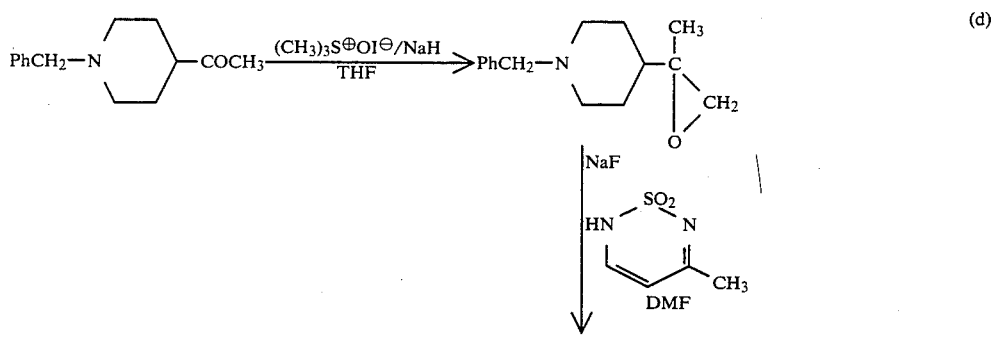

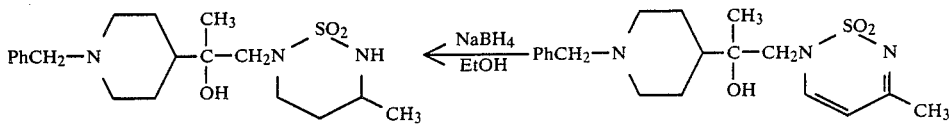

Starting materials of the formula (III) in which the piperidine ring is substituted with a hydroxyl group in the 3-position can be prepared by conventional procedures. A typical route to such compounds, which is illustrated in detail in the following Preparations, is as follows:

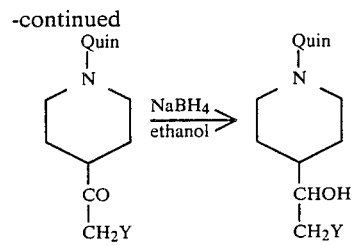

(e)

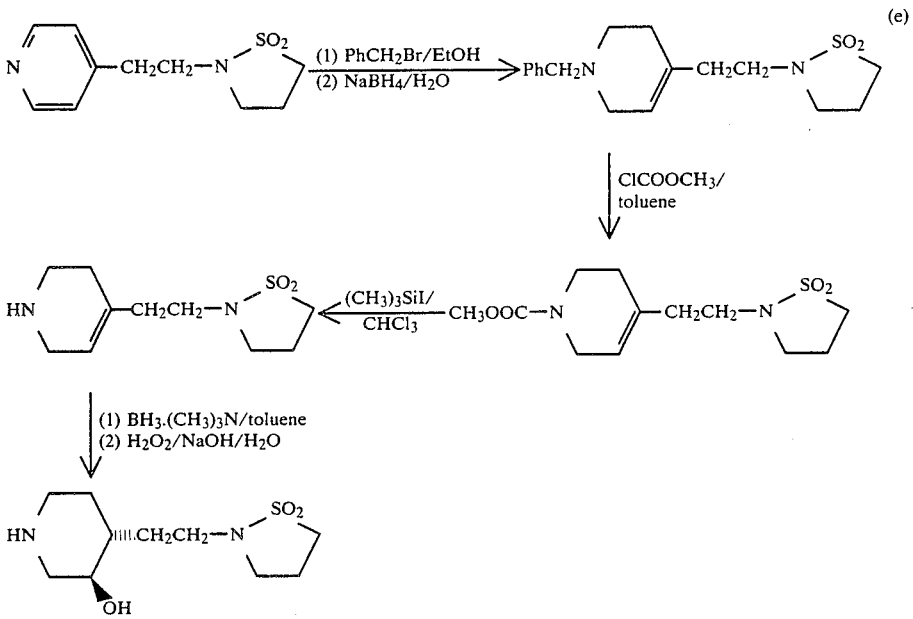

Routes to the pyridine and N-benzyl-piperidine starting materials for this method are described in published European application No. 0094766 already referred to herein.

Route B

Compounds of the invention in which X is —CH(OH)CH$_2$— can be prepared by this route, which is illustrated in general terms as follows, where "Quin" represents a 6,7-dimethoxyquinazolin-4-yl group:

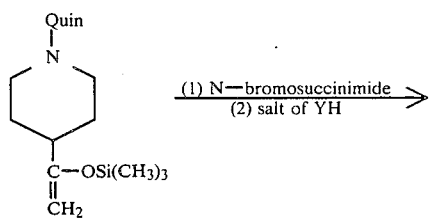

Preferably the salt of YH has the formula $M^{\oplus}Y^{\ominus}$ where M is Na, K, Li or n-Bu$_4$N. The first step in this route involves the bromination of the silyl ether to give the α-bromoketone which is not isolated, followed by displacement of bromide ion by the anion $Y^{\ominus}$. Typically, the reaction is carried out at room temperature in a suitable organic solvent and the products can be isolated and purified by conventional procedures. The starting materials are either known compounds or are obtainable conventionally. The sodium salts can for example be obtained by reacting the appropriate heterocyclic compound YH with sodium hydride in dimethylformamide. Again the quinazoline starting material is preparable conventionally, e.g. as follows:

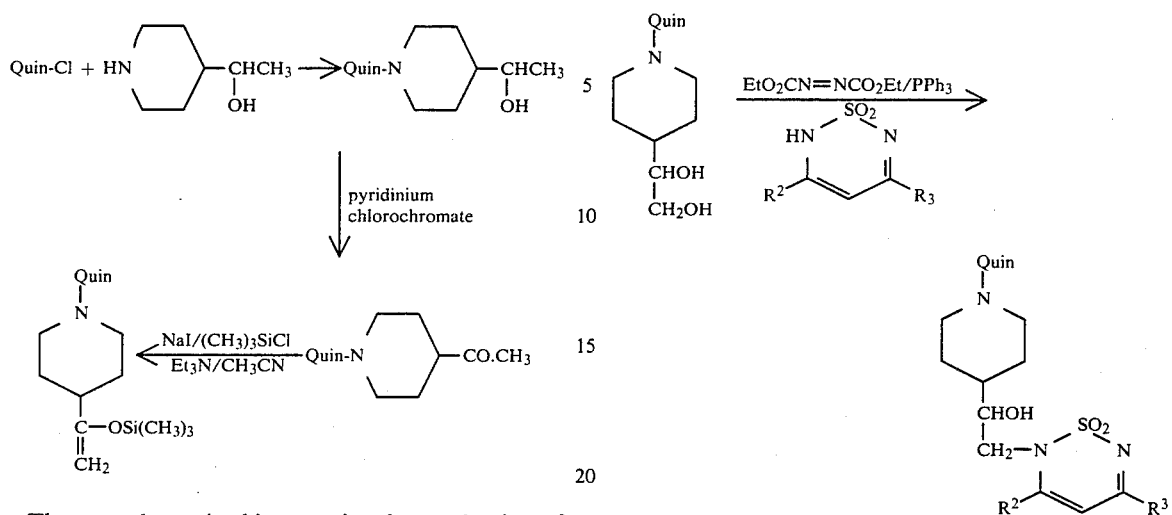

The second step in this route involves reduction of the carbonyl group with sodium borohydride. This step will also reduce certain heterocyclic groups Y, e.g. in the following illustration:

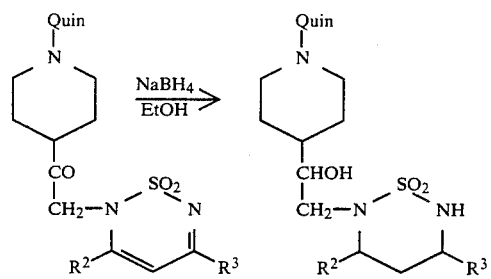

(where $R^2$ and $R^3$ are as previously defined). The reaction is typically carried out at room temperature.

Route C

The compounds of the formula (I) in which Y is

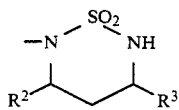

can be prepared by the selective reduction of the corresponding compounds in which Y is

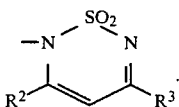

The reduction is typically carried out using sodium borohydride in ethanol at room temperature.

Route D

Compounds of the invention in which X is —CH(OH)CH$_2$— can also be prepared by this route, which is illustrated as follows:

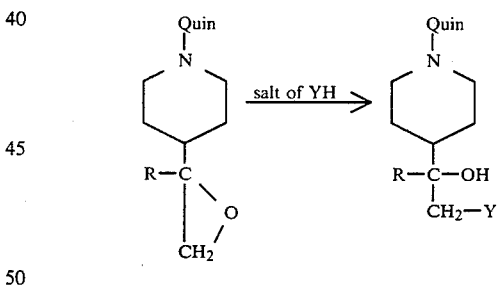

(where $R^2$ and $R^3$ are as previously defined). The reaction can be carried out in a suitable organic solvent, e.g. THF, at room temperature. If necessary, heating at up to reflux temperature can be used to accelerate the reaction.

The starting material for this route is prepared by the method of Route A from the compound of formula (II) and the appropriately substituted piperidine.

Route E

Compounds of the invention in which X is —CR(OH)CH$_2$—, where R is H, CH$_3$ or C$_2$H$_5$, can also be prepared by this route, which is illustrated in general terms as follows:

Preferably the said salt has the formula $M^{\oplus}Y^{\ominus}$ where M is Na, K, Li or n-Bu$_4$N.

Thus it can be seen that this reaction involves the nucleophilic opening of the epoxide by the anion $Y^{\ominus}$.

Typically the reactions are carried out at 100° C. in a suitable organic solvent, e.g. DMF and are typically complete in 6 hours or less. The products can then be isolated and purified by conventional methods. The starting materials are either known compounds or are obtainable conventionally. The sodium salts can for example be obtained by reacting the appropriate heterocyclic compound YH with sodium hydride in DMF solvent. The potassium salts are generated in situ by reaction of the appropriate heterocycle with potassium fluoride. Again the quinazoline starting materials are preparable conventionally, e.g. as follows:

(a)
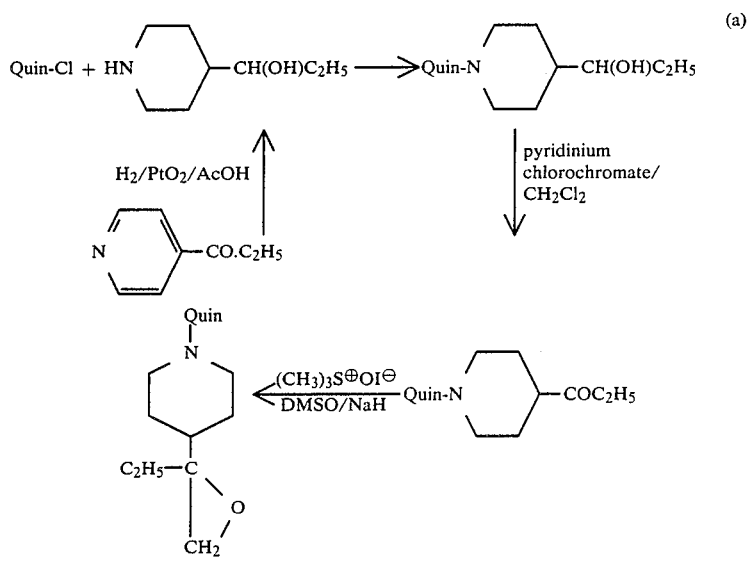
(b)
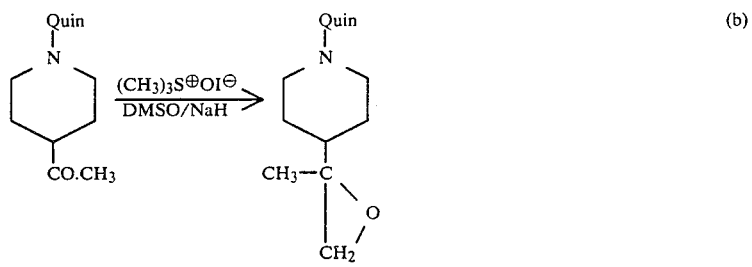
(c)
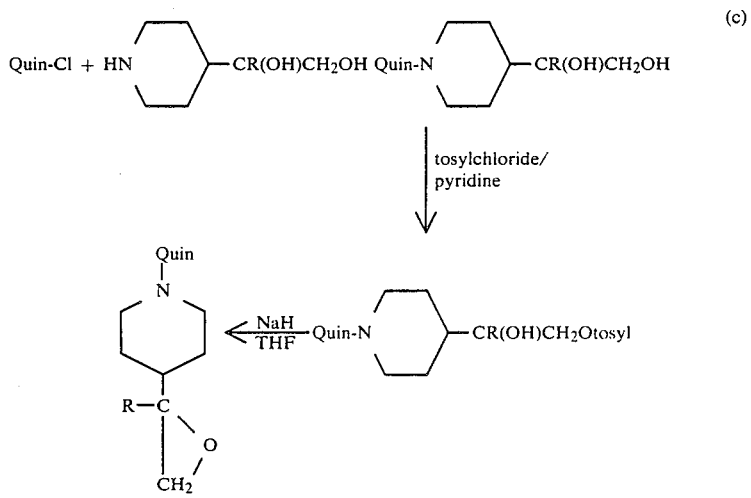
Route F
This route, to compounds in which the piperidino group is substituted with a hydroxyl group in the 4-position, is illustrated in general terms as follows:
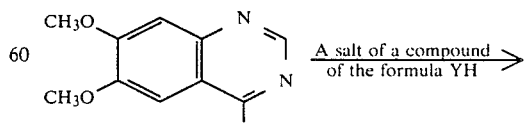
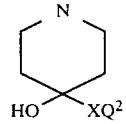

-continued

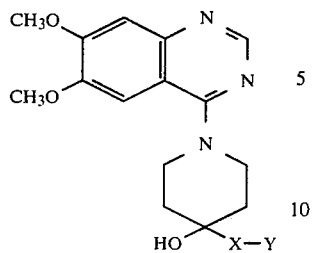

wherein $Q^2$ is a facile leaving group, e.g., Cl, Br, I or -O.Tosyl. Preferably said salt has the formula $M^{\oplus}Y^{\ominus}$ where M is Na, K, Li or n-Bu$_4$N.

Thus it will be seen that this reaction essentially involves the displacement of a facile leaving group by the anion $Y^{\ominus}$.

Typical reactions can be represented as follows:

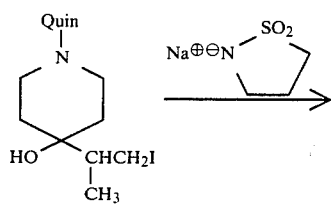
(a)

(b)

Typically the reactions are carried out at 80° C. in a suitable organic solvent, e.g. dimethylformamide, and the products can then be isolated and purified by conventional procedures.

The starting materials are either known compounds or are obtainable conventionally. The sodium salts $Na^{\oplus}Y^{\ominus}$ can for example be obtained by reacting the appropriate heterocyclic compound YH with sodium hydride. The quinazoline starting materials are preparable conventionally, e.g. as follows:

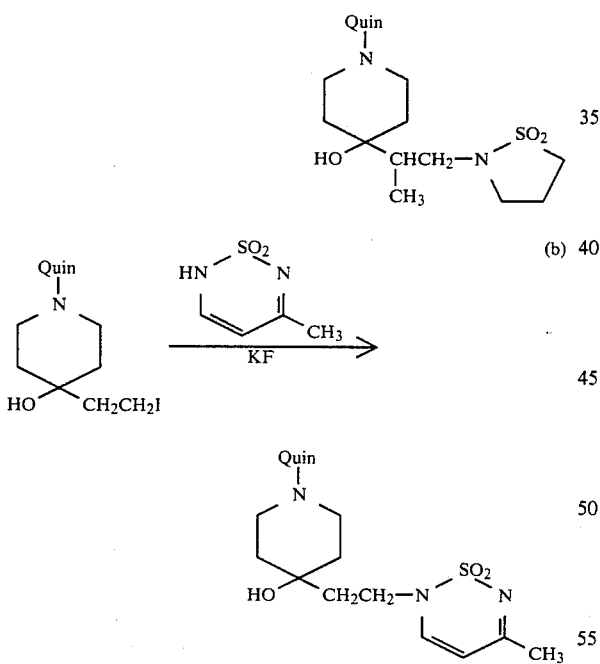

The piperidine starting materials for Routes B, D, E and F are either known compounds or can be prepared by conventional methods from the corresponding pyridines.

Route G

This route, to compounds in which the piperidino group is substituted with a hydroxy group in the 3-position, is illustrated in general terms as follows:

where T is a t-butyl-dimethylsilyl or equivalent protecting group.

Typically, the desired compound, with the 3-hydroxy group on the piperidine ring suitably protected by a t-butyl-dimethylsilyl group, is treated in a suitable organic solvent, e.g. acetonitrile, with 40% aqueous hydrofluoric acid at room temperature, for a sufficient period to remove the protecting group, then treated with aqueous saturated sodium carbonate solution, and isolated and purified by conventional procedures.

The starting materials are prepared by the methods of the preceding Routes D or F, e.g. as follows:

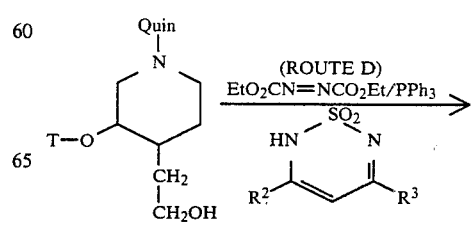

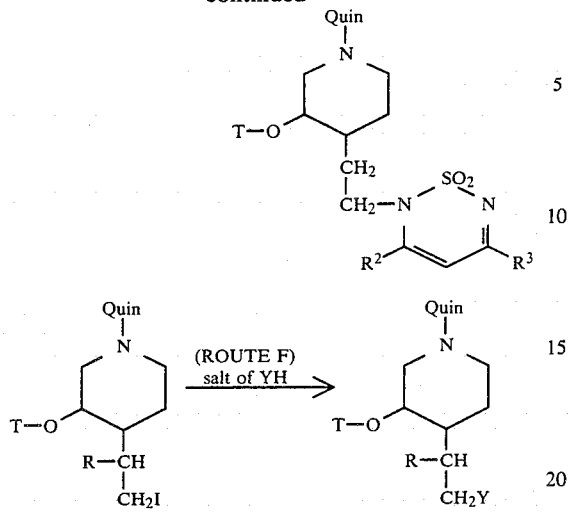

The starting materials for these methods are themselves prepared by the method of Route A from the compound of formula (II) and the appropriate protected 3-hydroxypiperidine, or by the methods already described for preparing starting materials for Route F. e.g. as follows:

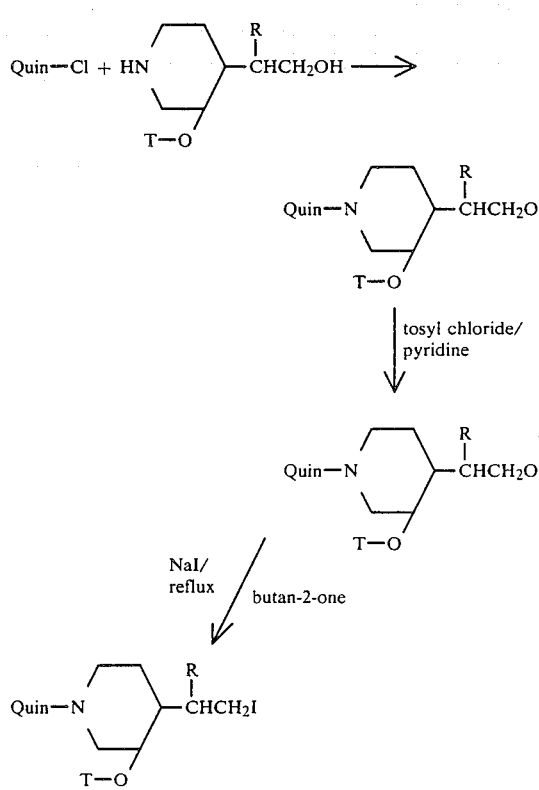

The 3-(T-protected hydroxy)piperidines are prepared by the following methods:

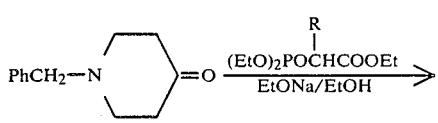

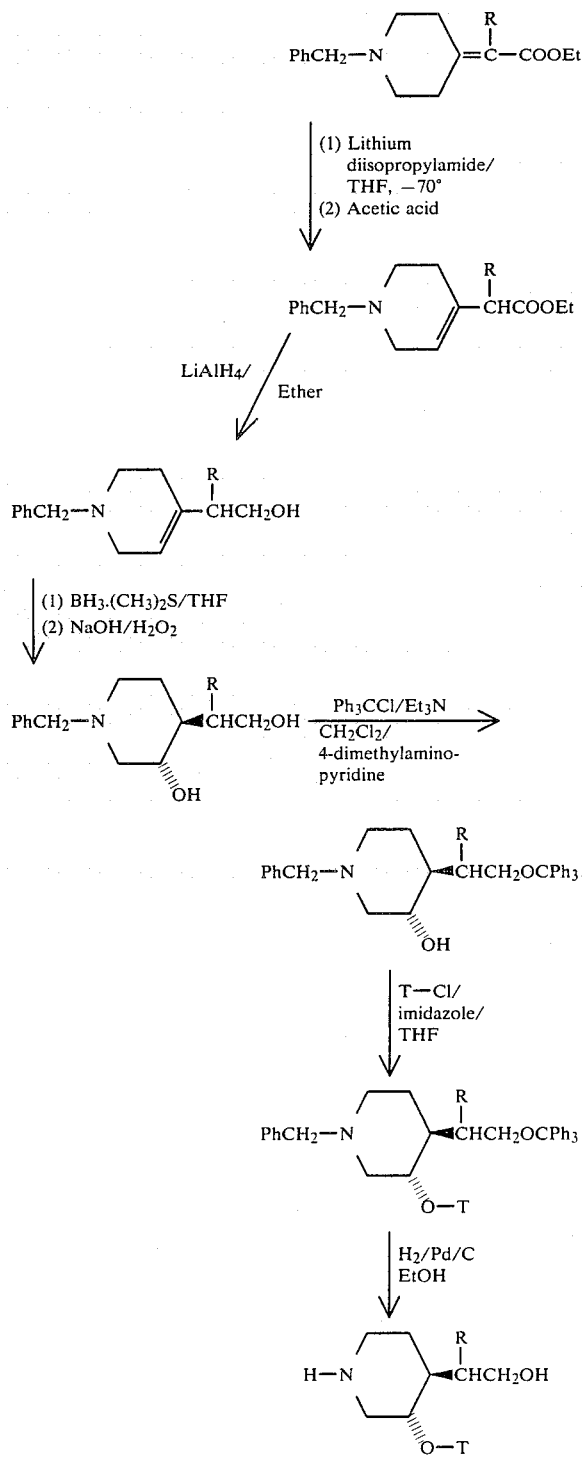

Where the compounds of the invention contain one or more asymmetric centres, then the invention includes the separated enantiomers and diastereoisomers or mixtures thereof. The separated forms can be obtained by conventional means.

The following Examples illustrate the invention (all temperatures in °C.):

EXAMPLE 1

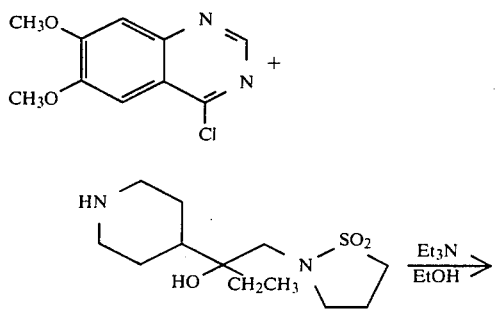

chloroform, 1:49 by volume, to give a solid which was recrystallised from ethyl acetate to afford 2-{2-hydroxy-2-[1-(6,7-dimethoxyquinazolin-4-yl)piperid-4-yl)]but-1-yl}isothiazolidine-1,1-dioxide, m.p. 171.5°–173.5° (0.25 g).

Analysis %: Found: C,56.5; H,6.9; N,11.7; Calculated for $C_{22}H_{32}N_4O_5S$: C,56.9; H,6.9; N,12.1.

EXAMPLES 2 TO 5

The following compounds were prepared similarly to Example 1, starting from 4-chloro-6,7-dimethoxyquinazoline, triethylamine and the appropriate piperidine (either as the free base or hydrochloride or acetate salt, according to the form in which the piperidines were prepared—see Preparations 4, 5 and 8). In cases where a salt of the piperidine is used, excess triethylamine is employed.

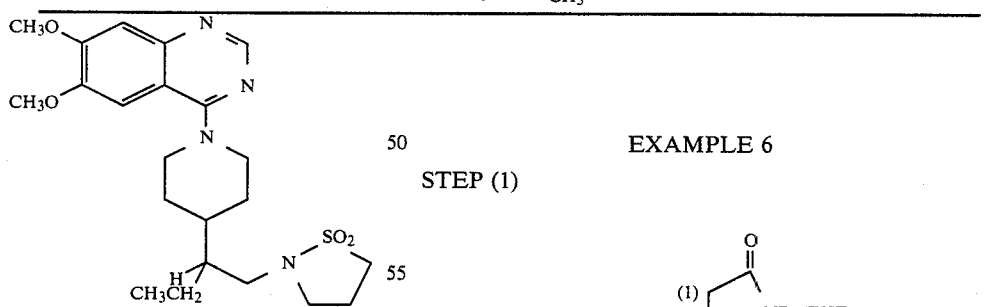

| Example No. | A | B | X—Y | Form isolated and m.p. | Analysis % (Theoretical in brackets) | | |
|---|---|---|---|---|---|---|---|
| | | | | | C | H | N |
| 2 | —H | —H | $-\overset{CH_3}{\underset{OH}{\overset{|}{C}}}CH_2N\overset{SO_2}{\diagdown}$ | Free base, 173–174° | 56.0 (56.0 | 6.9 6.7 | 12.3 12.4) |
| 3 | —OH | —H | $-CH_2CH_2N\overset{SO_2}{\diagdown}$ | Free base, 149–152° | 55.0 (55.0 | 6.6 6.5 | 13.2 12.8) |
| 4 (Diasteromer A) 5 (Diastereomer B) | —H | —H | $-\overset{CH_3}{\underset{OH}{\overset{|}{C}}}CH_2N\overset{SO_2}{\diagdown}\text{NH}\ldots CH_3$ | Free base, 188–190° Free base, 219–222.5° | 54.7 (55.1 54.9 (55.1 | 7.1 6.9 6.9 6.9 | 14.4 14.6) 14.5 14.6) |

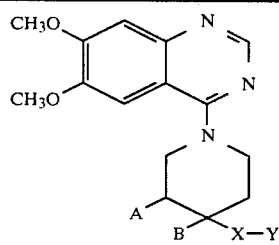

4-Chloro-6,7-dimethoxyquinazoline (0.224 g), 2-[2-hydroxy-2-(piperid-4-yl)but-1-yl]isothiazolidine-1,1-dioxide (0.274 g) and triethylamine (1 cm³) were heated together under reflux in ethanol (10 cm³) for 4 hours. After cooling, volatile material was removed in vacuo, the residue partitioned between chloroform (30 cm³) and water (10 cm³) and the aqueous phase was further extracted with chloroform (2×20 cm³). The combined dried (MgSO₄) organic extracts were evaporated and the residue chromatographed on silica ("Merck"[Trademark] 60.9385) eluting with methanol:-

EXAMPLE 6

STEP (1)

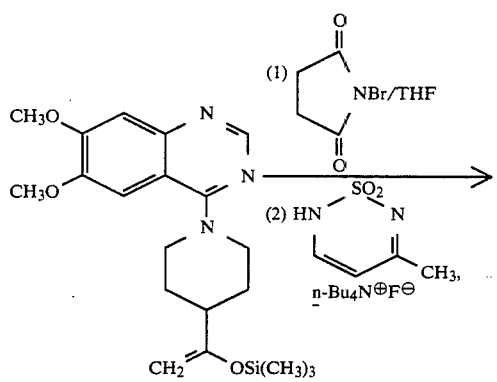

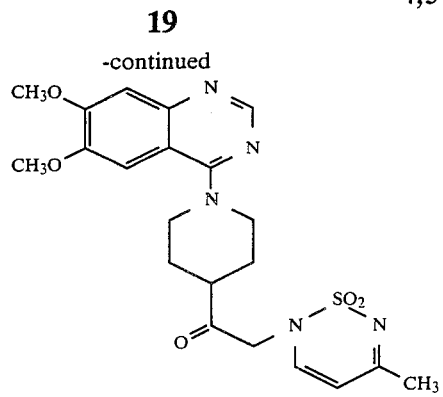

A solution of 6,7-dimethoxy-4-[4-(1-trimethylsilyloxy)ethenylpiperid-1-yl]quinazoline (3.87 g) in THF (20 cm³) was treated at 0° with N-bromosuccinimide (1.78 g). The solution was treated after 20 minutes with a solution of 2H-5-methyl-1,2,6-thiadiazine-1,1-dioxide (2.2 g) in THF (20 cm³) followed by tetrabutylammonium fluoride (15.0 cm³ of a 1M solution in THF) and the mixture was stirred for 16 hours at room temperature. Volatile material was removed in vacuo and the residue was partitioned between ethyl acetate (100 cm³) and water (50 cm³). The dried (MgSO₄) organic layer was evaporated and the residue chromatographed on silica ("Merck" 60.9385) eluting with chloroform to give a foam which was crystallised from ethyl acetate to give 2-{2-oxo-2-[1-(6,7-dimethoxyquinazolin-4-yl)piperid-4-yl]ethyl}-5-methyl-1,2,6-thiadiazine-1,1-dioxide, m.p. 172°–175° (2.0 g).

Analysis %: Found: C,54.7; H,5.5; N,15.3; Calculated for $C_{21}H_{25}N_5O_5S$: C,54.9; H,5.5; N,15.2.

STEP (2)

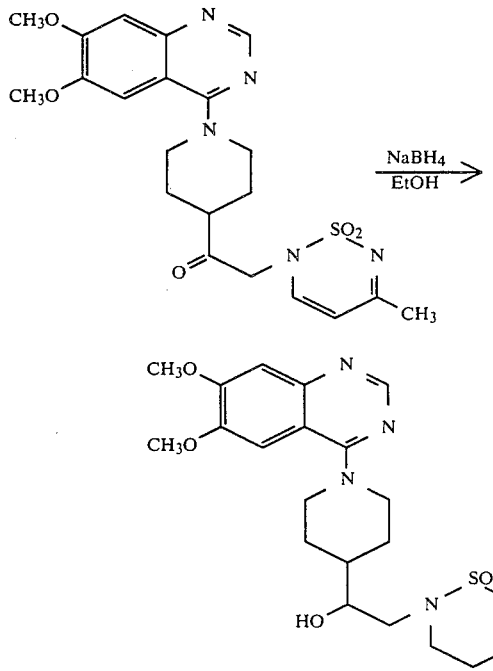

Sodium borohydride (40 mg) was added at 0° to a stirred solution of 2-{2-oxo-2-[1-(6,7-dimethoxyquinazolin-4-yl)piperid-4-yl]ethyl}-5-methyl-1,2,6-thiadiazine-1,1-dioxide (0.4 g) in ethanol (10 cm³). After 2 hours the volatile material was removed in vacuo and the residue was partitioned between water (10 cm³) and dichloromethane (20 cm³). The dried organic extract was evaporated to give a solid which was chromatographed on silica ("Merck" 60.9385) eluting with methanol:chloroform, 1:19, to give a foam which was crystallised from ethyl acetate to afford 2-{2-hydroxy-2-[1-(6,7-dimethoxyquinazolin-4-yl)piperid-4-yl]ethyl}-5-methyltetrahydro-1,2,6-thiadiazine-1,1-dioxide as microcrystals, m.p. 189°–193° (0.30 g).

Analysis %: Found: C,53.9; H,6.9; N,15.0 Calculated for $C_{21}H_{31}N_5O_5S$: C,54.2; H,6.7; N,15.0.

EXAMPLE 7

The following compound was prepared similarly to the previous example, starting from 6,7-dimethoxy-4-[4-(1-trimethylsilyloxy)ethenylpiperid-1-yl]quinazoline and the tetrabutyl-ammonium derivative of the appropriate heterocycle.

STEP (1) product:

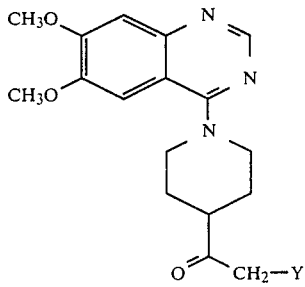

| Y | Form isolated and m.p. | Analysis % (Theoretical brackets) | | |
|---|---|---|---|---|
| | | C | H | N |
| —N(SO₂)N (ring with CH) | 0.25 hydrate, 184–187° | 53.5 (53.4 | 5.3 5.3 | 15.3 15.6) |

STEP (2) product:

| Y | Form isolated and m.p. | Analysis % (Theoretical brackets) | | |
|---|---|---|---|---|
| | | C | H | N |
| —N(SO₂)NH (ring with CH) | monohydrate 114° | 51.2 (51.2 | 6.2 6.6 | 14.5 14.9) |

EXAMPLE 8

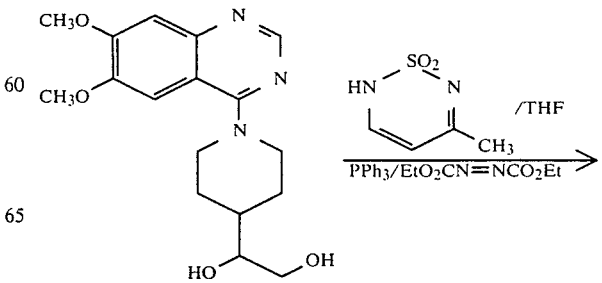

-continued

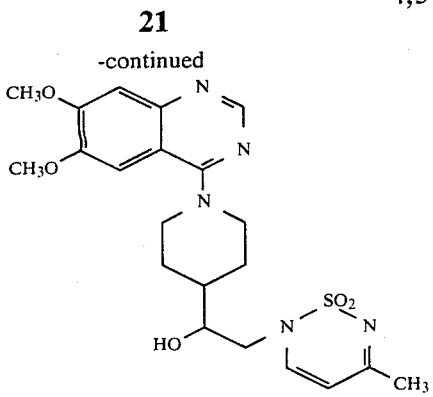

A mixture of 1-[1-(6,7-dimethoxyquinazolin-4-yl)piperid-4-yl]ethane-1,2-diol (1.33 g), triphenylphosphine (1.26 g) and 2H-5-methyl-1,2,6-thiadiazine-1,1-dioxide (0.70 g) was stirred in THF (10 cm³) at room temperature during the addition of diethylazodicarboxylate (0.75 cm³). After heating under reflux for 2 hours the volatile material was removed in vacuo and the residue was chromatographed on silica ("Merck" 60.9385) eluting with methanol:chloroform, 1:19, to give an oil which was crystallised from ethyl acetate to afford 2-{2-hydroxy-2-[1-(6,7-dimethoxyquinazolin-4-yl)piperid-4-yl)]ethyl}-5-methyl-1,2,6-thiadiazine-1,1-dioxide hemihydrate, m.p. 183°–185° (0.158 g).

Analysis %: Found: C,53.6; H,5.8; N,14.8; Calculated for $C_{21}H_{27}N_5O_5S \cdot 0.5H_2O$: C,53.6; H,6.0; H,14.9.

EXAMPLE 9

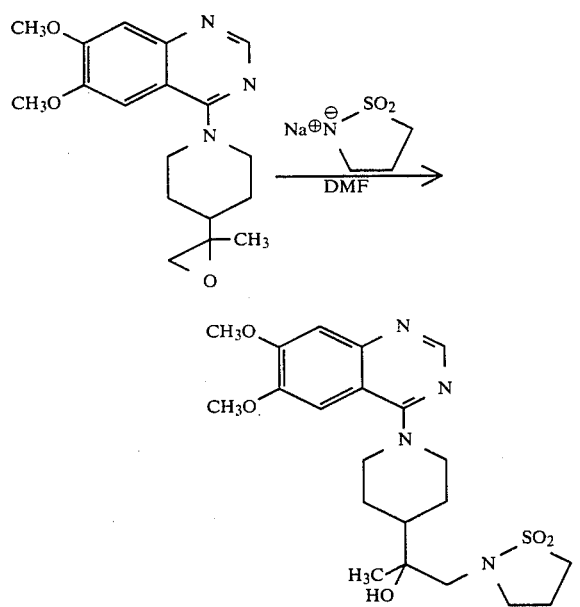

Sodium hydride (1.25 g of a 50% dispersion in oil) was added at room temperature to a stirred solution of isothiazolidine-1,1-dioxide (2.42 g) in DMF (15 cm³). After stirring for 0.5 hours 2-methyl-2-[1-(6,7-dimethoxyquinazolin-4-yl)piperid-4-yl]oxirane (5.0 g) was added and the mixture was stirred for 4 hours at 100°. Volatile material was removed in vacuo, the residue was partitioned between chloroform (100 cm³) and water (50 cm³) and the chloroform layer was dried (MgSO₄) and evaporated. The residue was chromatographed on silica ("Merck" 60.9385) eluting with methanol:ethyl acetate, 1:4, to give a solid which was recrystallised from ethyl acetate-methanol to give 2-{2-hydroxy-2-[1-(6,7-dimethoxyquinazolin-4-yl)piperid-4-yl]prop-1-yl}isothiazolidine-1,1-dioxide, m.p. 173°–174° (4.15 g).

Analysis %: Found: C,55.6; H,6.8; N,12.4; Calculated for $C_{21}H_{30}N_4O_5S$: C,56.0; H,6.7; N,12.4.

EXAMPLES 10 TO 13

The following Examples were similarly prepared to the previous Example starting from the appropriate oxirane and the appropriate heterocycle in the presence of potassium fluoride (Examples 10 and 12) or sodium hydride (Examples 11 and 13) as base.

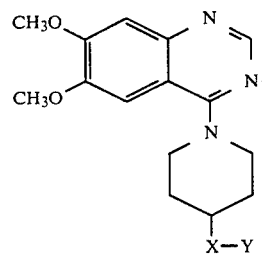

| Example No. | X—Y | Form isolated and m.p. | Analysis % (Theoretical in brackets) | | |
|---|---|---|---|---|---|
| | | | C | H | N |
| 10 | OH, —CCH₂N(SO₂)N, CH₃ ... CH₃ | Free base 225–227° | 55.3 (55.6 | 6.15 6.15 | 14.5 14.7) |
| 11 | OH, —CHCH₂N(SO₂) | Free base, 129–132° | 55.1 (55.0 | 6.3 6.5 | 13.2 12.8) |
| 12 | Et, —CCH₂N(SO₂), OH | Free base, 170–172° | 56.9 (56.9 | 7.0 6.9 | 11.7 12.1) |
| 13 | Et, —CCH₂N(SO₂)N, OH ... CH₃ | Free base, 166.5–170.5° | 56.7 (56.4 | 6.5 6.4 | 14.0 14.3) |

EXAMPLE 14

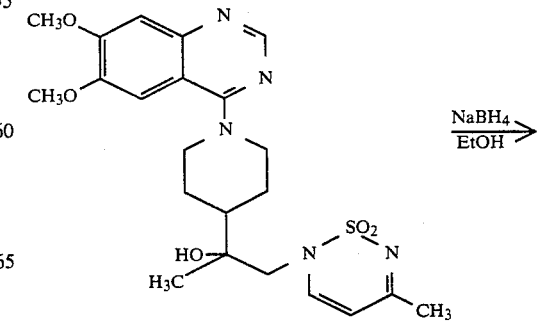

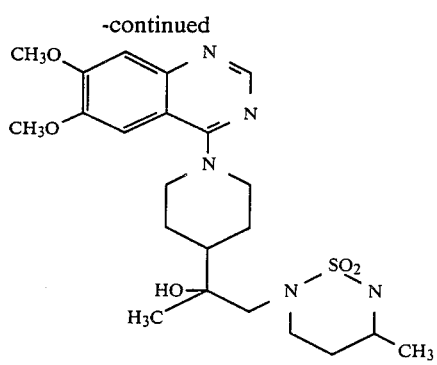

Sodium borohydride (0.070 g) was added at room temperature to a stirred solution of 2-{2-hydroxy-2-[1-(6,7-dimethoxyquinazolin-4-yl)piperid-4-yl]prop-1-yl}-5-methyl-1,2,6-thiadiazine-1,1-dioxide (0.46 g) in ethanol (10 cm³). After 1 hour 2M hydrochloric acid (1 cm³) was added, volatile material was removed in vacuo and the residue was partitioned between chloroform (20 cm³) and 1M sodium hydroxide solution (10 cm³). The aqueous phase was extracted further with chloroform (2×10 cm³) and the combined organic extracts were dried (MgSO₄) and evaporated to give an oil. Chromatography on silica ("Merck" 60.9385) eluting with methanol:ethyl acetate, 1:9, gave a solid (0.45 g) which was re-crystallised from ethyl acetate to afford 2-{2-hydroxy-2-[1-(6,7-dimethoxyquinazolin-4-yl)piperid-4-yl]prop-1-yl}-5-methyltetrahydro-1,2,6-thiadiazine-1,1-dioxide, m.p. 207°–209° (0.11 g). Examination of the ¹H NMR spectrum at 250 MHz showed the compound to be a mixture of diastereomers.

Analysis %: Found: C,54.7; H,6.9; N,14.4; Calculated for $C_{22}H_{33}N_5O_5S$: C,55.1; H,6.9; N,14.6.

EXAMPLES 15 TO 20

The following examples were prepared similarly to the previous example starting from the appropriate 1,2,6-thiadiazine-1,1-dioxide derivative.

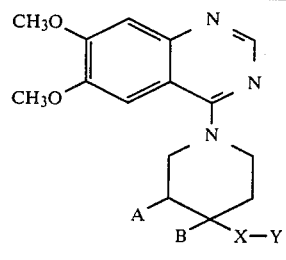

| Example No. | A | B | —X—Y | Form Isolated and m.p. (°C.) | Analysis % (Theoretical in brackets) C | H | N |
|---|---|---|---|---|---|---|---|
| 15 | —H | —OH | —CH₂CH₂N(SO₂)(NH)(CH₃) | Free base, 229.5–231° | 54.3 (54.2 | 6.7 6.7 | 14.9 15.0) |
| 16 | —H | —OH | —CH(CH₃)CH₂N(SO₂)(NH)(CH₃) | 0.5 H₂O, 108–115° | 54.1 (54.1 | 6.9 7.0 | 14.0 14.3) |
| 17 | —H | —H | —C(Et)(OH)CH₂N(SO₂)(NH)(CH₃) | Free base, 197–202° | 56.0 (56.0 | 7.5 7.2 | 14.3 14.2) |
| 18 | —OH | H | —CH₂CH₂N(SO₂)(NH)(CH₃) | Free base, 194–195° | 53.8 (54.2 | 6.6 6.7 | 15.1 15.0) |
| 19 (Diastereomer A) | | | —CH(CH₃)CH₂N(SO₂)(NH)(CH₃) | Free base, 220–223° | 54.7 (55.1 | 6.8 6.9 | 14.3 14.6 |
| 20 (Diastereomer B) | —OH | H | | Crude solid, foam | — | | |

EXAMPLE 21

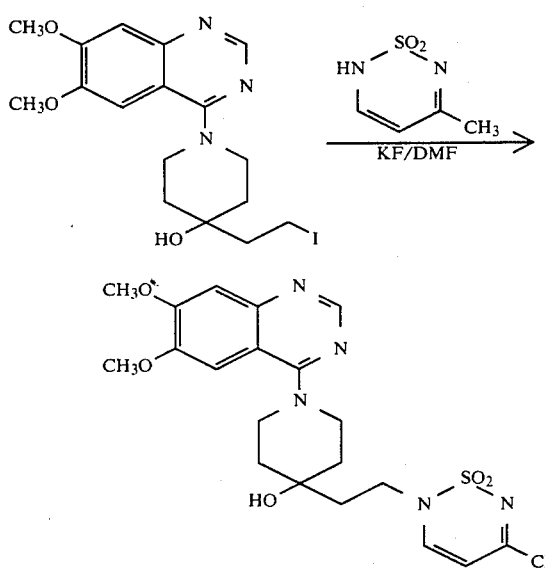

A mixture of 6,7-dimethoxy-4-[4-hydroxy-4-(2-iodoethyl)piperid-1-yl]quinazoline (0.22 g), potassium fluoride (0.06 g) and 2H-5-methyl-1,2,6-thiadiazine-1,1-dioxide (0.15 g) was heated at 80° with stirring for 4 hours in DMF. Volatile material was removed in vacuo, the residue was partitioned between water (10 cm$^3$) and chloroform (50 cm$^3$) and the dried (MgSO$_4$) organic phase was evaporated to give an oil. Chromatography on silica ("Merck" 60.9385) eluting with methanol:-chloroform, 1:50, gave a foam which crystallised from ethyl acetate to afford 2-{2-[1-(6,7-dimethoxyquinazolin-4-yl)-4-hydroxy-piperid-4-yl]ethyl}-5-methyl-1,2,6-thiadiazine-1,1-dioxide, m.p. 203°–204° (0.13 g).

Analysis %: Found: C,54.5; H,5.9; N,14.5; Calculated for C$_{21}$H$_{27}$N$_5$O$_5$S: C,54.6; H,5.9; N,15.2.

EXAMPLES 22 TO 24

The following Examples were prepared similarly to Example 21 starting from the appropriate 6,7-dimethoxy-4-(4-hydroxy-4-iodoalkyl-piperidyl)quinazoline and using the sodium salt of the appropriate heterocycle.

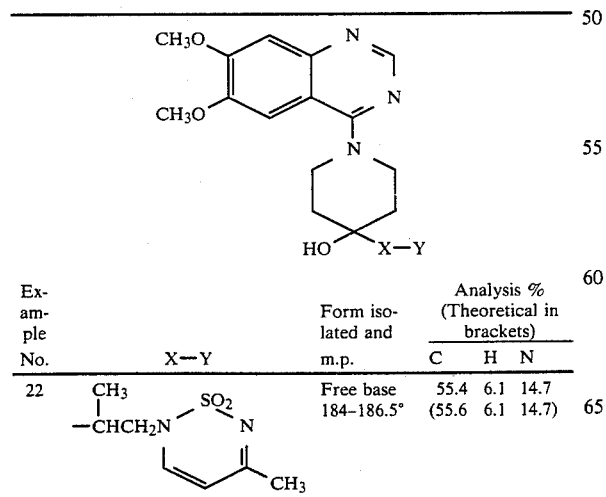

| Example No. | X—Y | Form isolated and m.p. | Analysis % (Theoretical in brackets) C | H | N |
|---|---|---|---|---|---|
| 22 | —CHCH$_2$N(CH$_3$)—SO$_2$—N=CH—CH=CH— (with CH$_3$) | Free base 184–186.5° | 55.4 (55.6) | 6.1 (6.1) | 14.7 (14.7) |
| 23 | —CH$_2$CH$_2$N(SO$_2$)— (pyrrolidine sulfonamide) | Free base 175–177° | 54.9 (55.0) | 6.4 (6.5) | 12.7 (12.8) |
| 24 | —CHCH$_2$N(CH$_3$)SO$_2$— (pyrrolidine) | Free base 165–168° | 55.7 (56.0) | 6.6 (6.7) | 12.3 (12.4) |

EXAMPLE 25

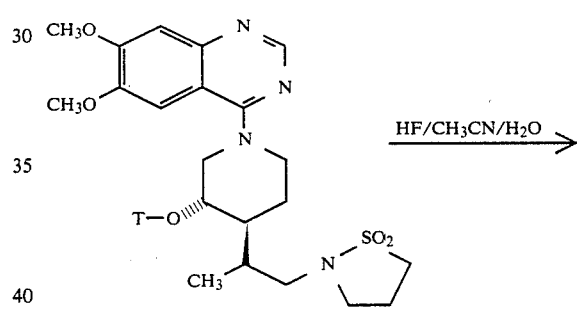

(Diastereomer A)

HF/CH$_3$CN/H$_2$O →

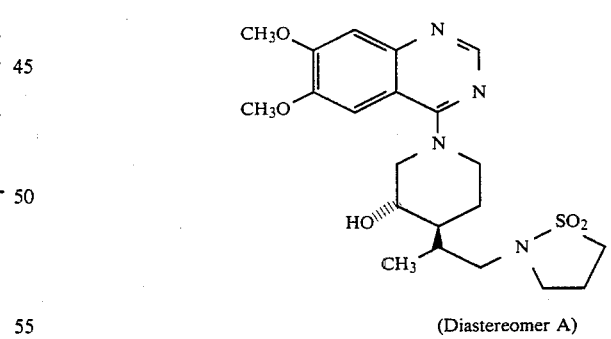

(Diastereomer A)

40% Aqueous hydrofluoric acid (0.5 cm$^3$) was added at room temperature to a stirred solution of trans-2-{2-[1-(6,7-dimethoxyquinazolin-4-yl)-3-t-butyldimethylsilyloxypiperid-4-yl]prop-1-yl}isothiazolidine-1,1-dioxide (diastereomer A; 0.64 g) in acetonitrile (7.0 cm$^3$). After stirring for 16 hours aqueous saturated sodium carbonate solution (5 cm$^3$) was added and the residue was partitioned between water (10 cm$^3$) and chloroform (60 cm$^3$). The dried (MgSO$_4$) organic layer was evaporated and the residue was chromatographed on silica ("Merck" 60.9385) eluting with chloroform to afford a foam which crystallised from ethyl acetate to give trans-2-{2-(1-[6,7-dimethoxy quinazolin-4-yl]-3-hydroxypiperid-4-yl)prop-1-yl}isothiazolidine-1,1-dioxide as microcrystals (diastereomer A) m.p. 173°–174° (0.394 g).

Analysis %: Found: C,55.9; H,6.7; N,12.6; Calculated for $C_{21}H_{30}N_4O_5S$: C,56.0; H,6.7; N,12.4.

EXAMPLES 26 TO 29

The following compounds were prepared similarly to Example 25 starting from trans-2-{2-[1-(6,7-dimethoxyquinazolin-4-yl)-3-t-butyl-dimethylsilyloxypiperid-4-yl]prop-1-yl}isothiazolidine-1,1-dioxide (diastereomer B) (Example 26);

trans-2-{2-[1-(6,7-dimethoxyquinazolin-4-yl)-3-t-butyldimethylsilyloxypiperid-4-yl]ethyl}-5-methyl-1,2,6-thiadiazine-1,1-dioxide (Example 27);

trans-2-{2-[1-(6,7-dimethoxyquinazolin-4-yl)-3-t-butyldimethylsilyloxypiperid-4-yl]prop-1-yl}-5-methyl-1,2,6-thiadiazine-1,1-dioxide (diastereomer A, Example 28; diastereomer B, Example 29).

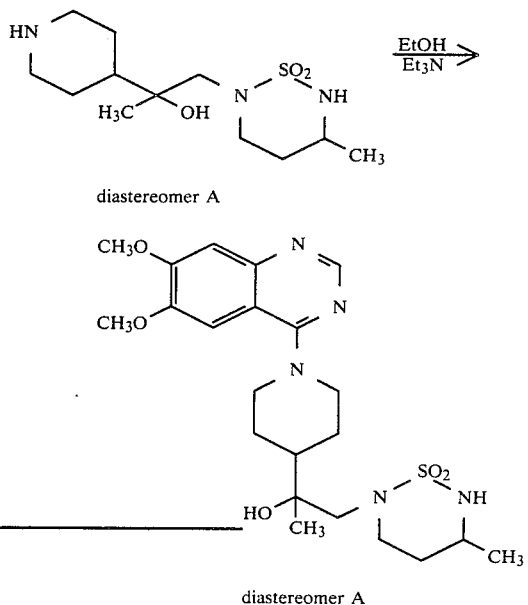

diastereomer A diastereomer A

| Example No. | R | Y | Form Isolated and m.p. (°C.) | Analysis % (Theoretical in brackets) | | |
|---|---|---|---|---|---|---|
| | | | | C | H | N |
| 26 (Diastereomer B) | CH₃ | —N(SO₂)(CH₂CH₂CH₂) | crude solid, foam >75° | — | | |
| 27 | H | —N(SO₂)N=CH–CH=C(CH₃)– | monohydrochloride 131–133° | 50.4 (50.6 | 5.7 5.7 | 13.7 14.1) |
| 28 (Diastereomer A) 29 (Diastereomer B) | CH₃ | —N(SO₂)N=C(CH₃)–CH=CH– | monohydrochloride hemihydrate, 147–150° Free base, 207–209° | 55.4 (55.6 | 6.3 6.2 | 14.7 14.7) |

EXAMPLE 30

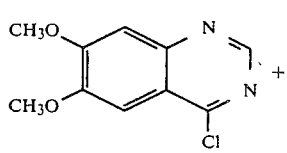

+

A mixture of 2-[2-(4-piperidyl)-2-hydroxy]prop-1-yl-5-methyltetrahydro-1,2,6-thiadiazine-1,1-dioxide, diastereomer A (1.28 g), 4-chloro-6,7-dimethoxyquinazoline (0.99 g) and triethylamine (2.1 cm³) in ethanol (21 cm³) was heated under reflux for 4 hours. The solution was evaporated, the residue dissolved in chloroform (5 cm³), and chromatographed on Merck 70–230 mesh Kieselgel 60 (100 g), eluting with chloroform:methanol, 19:1. Evaporation of the combined requisite fractions gave 2-[2-hydroxy-2-{1-(6,7-dimethoxyquinazolin-4- yl)piperidin-4-yl}prop-1-yl]-5-methyltetrahydro-1,2,6-thiadiazine-1,1-dioxide, diastereomer A (1.90 g, 90.2%) as off white crystals, m.p. 186°-188° C., identical to the product of Example 4.

The following preparations illustrate the synthesis of certain of the starting materials. All temperatures are in °C.

Preparation 1

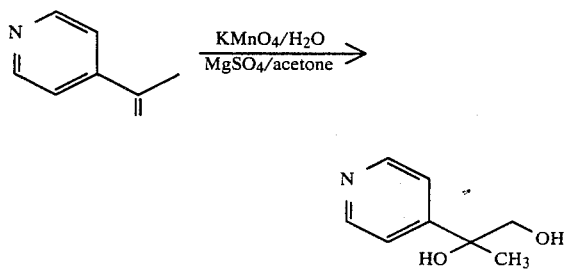

A solution of potassium permanganate (10.6 g) and magnesium sulphate (4.0 g) in water (250 cm³) was added at 0° to a mechanically stirred solution of 4-isopropenyl pyridine (14.8 g) in acetone (150 cm³) over 0.5 hours. After a further 0.5 hours at 0°, the mixture was warmed to room temperature over 1 hour, hydroquinone (0.01 g) was added and the mixture was filtered through "Avicel" (Trademark) to remove manganese dioxide. Solvents were removed in vacuo yielding a viscous oil which was chromatographed on silica ("Merck" 60.9385) eluting with methanol:chloroform, 1:19, to give 2-(4-pyridyl)propan-1,2-diol as an oil (6.0 g).

Preparation 2

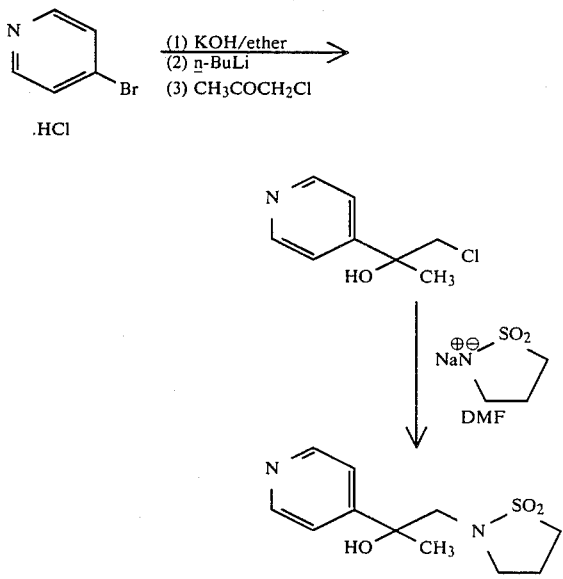

A mixture of 4-bromopyridine hydrochloride (3.8 g) and potassium hydroxide (1.1 g) was stirred at room temperature in anhydrous ether (20 cm³) for 0.5 hours. The mixture was then cooled −70°, n-BuLi (12.2 cm³ of a 1.6M solution in hexane) was added, the mixture was stirred for 1 hour and chloroacetone (1.39 g) in ether (10 cm³) was added. Stirring was continued for 1 hour, acetic acid (1.2 g) was added and the mixture was partitioned between sodium carbonate solution and ether. The organic phase was dried (MgSO₄) and evaporated and the residue was chromatographed on silica ("Merck" 60.9385) eluting with ethyl acetate:petrol (b.p. 60°-80°), 2:3, to give 2-(4-pyridyl)-2-hydroxypropylchloride as a waxy solid (0.6 g). This material was taken without further purification into DMF (5 cm³) and this was then added to a solution of 2-sodioisothiazolidine-1,1-dioxide [made from isothiazolidine-1,1-dioxide (0.65 g) and sodium hydride (0.5 g of a 50% dispersion in oil) in DMF (10 cm³)] and the mixture was heated for 3 hours at 130°. Volatile material was removed in vacuo, the residue was partitioned between chloroform and water, the aqueous phase was extracted further with chloroform (2×25 cm³) and the combined extracts were dried (MgSO₄) and evaporated to afford an oil. Chromatography on silica ("Merck" 60.9385) eluting with methanol:chloroform, 1:19, gave 2-[2-(4-pyridyl)-2-hydroxy]prop-1-ylisothiazolidine-1,1-dioxide as an oil (0.48 g) which was used without further purification.

Preparation 3

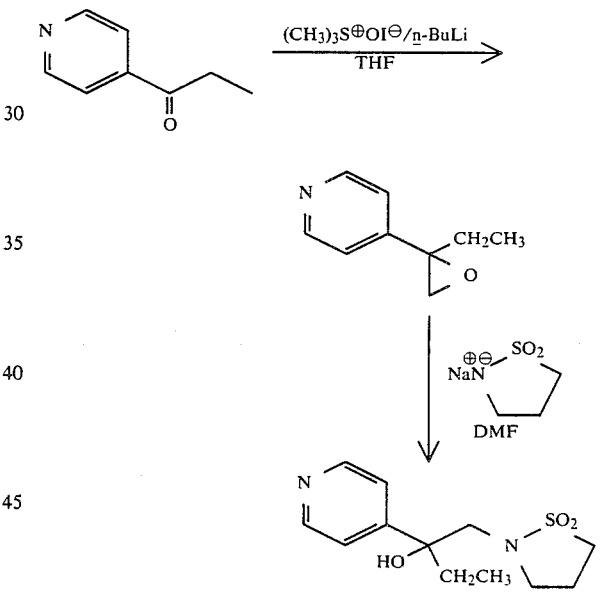

n-Butyl lithium (7.3 cm³ of a 1.6M solution in hexane) was added at 0° to a stirred suspension of trimethyl sulphonium iodide (2.45 g) in THF (40 cm³) under nitrogen. After 5 minutes 4-propionylpyridine (1.35 g) in THF (5 cm³) was added, the mixture was allowed to warm to room temperature over 1.5 hours, water (20 cm³) was added and volatile material was removed in vacuo. The residue was partitioned between ether and water, the ethereal layer was dried (MgSO₄) and evaporated and the residue was chromatographed on silica ("Merck" 60.9385) eluting with methanol:chloroform, 1:49, to give 2-ethyl-2-(4-pyridyl)oxirane as an oil (0.6 g). This material was taken without further purification into DMF (5 cm³) and treated with a solution of 2-sodioisothiazolidine-1,1-dioxide [made from isothiazolidine-1,1-dioxide (0.6 g) and sodium hydride (0.30 g of a 50% dispersion in oil)] in DMF (2 cm³) at 100° for 4 hours. Volatile material was removed in vacuo, the residue was partitioned between ethyl acetate (20 cm³) and water (10 cm³) and the aqueous phase was further extracted with ethyl acetate (2×20 cm³). The combined extracts were dried (MgSO₄) and evaporated, and the residue was chromatographed on silica ("Merck" 60.9385) eluting with methanol:chloroform, 1:49, to afford 2-[2-(4-pyridyl)-2-hydroxy]but-1-ylisothiazolidine-1,1-dioxide as an oil.

Preparation 4

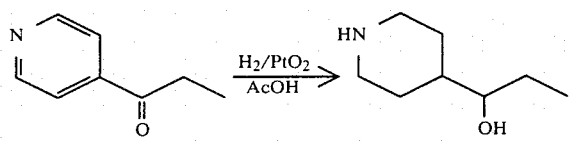

A solution of 4-propionyl pyridine (10.0 g) in acetic acid (100 cm³) was hydrogenated over platinum oxide (0.5 g) at 60° and 60 p.s.i. pressure for 60 hours. The mixture was filtered through "Avicel" and volatile material was removed in vacuo to give the crude acetate salt (12.0 g). A portion (1 g) was taken into chloroform (20 cm³), washed with 1M sodium hydroxide solution (10 cm³), dried and evaporated to afford 1-(4-piperidyl)propanol, m.p. 50° (0.70 g).

Analysis %: Found: C,66.5; H,11.9; N,9.7; Calculated for C₈H₁₇NO: C,67.1; H,12.0; N,9.7.

Preparation 5

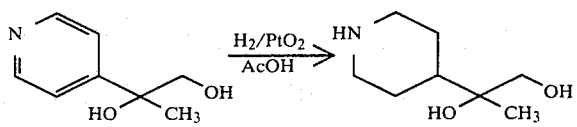

A solution of 2-(4-pyridyl)propane-1,2-diol (2.0 g) in acetic acid (30 cm³) was hydrogenated over platinum oxide (0.10 g) at 60° and 60 p.s.i. pressure for 16 hours. The catalyst was removed by filtration through "Avicel" and volatile material was removed in vacuo to afford 2-(4-piperidyl)propan-1,2-diol (2.1 g). (Crude acetate salt, oil).

Also prepared by a similar method from the appropriate pyridine starting materials were:

2-[2-(4-piperidyl)-2-hydroxy]prop-1-yl-isothiazolidine-1,1-dioxide (crude acetate salt, oil);
2-[2-(4-piperidyl)-2-hydroxy]but-1-yl-isothiazolidine-1,1-dioxide (crude acetate salt, oil);
2-[2-(4-piperidyl)-2-hydroxy]prop-1-yl-5-methyltetrahydro-1,2,6-thiadiazine-1,1-dioxide (Diastereomer A, crude acetate salt, oil); and
2-[2-(4-piperidyl)-2-hydroxy]prop-1-yl-5-methyl-tetrahydro-1,2,6-thiadiazine-1,1-dioxide (Diastereomer B, crude acetate salt, oil).

Preparation 6

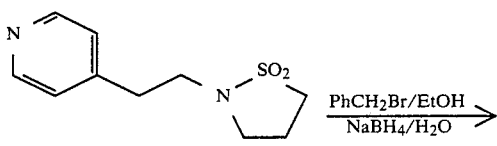

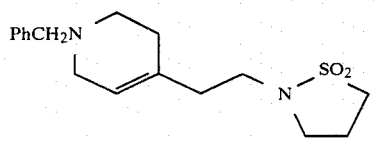

Benzyl bromide (3.1 cm³) was added at room temperature to a stirred solution of 2-[2-(4-pyridyl)ethyl]isothiazolidine-1,1-dioxide (4.9 g) in ethanol (30 cm³) and the mixture was heated under reflux for 3 hours. After cooling to room temperature, water (30 cm³) was added followed by sodium borohydride (1.2 g) and the mixture was stirred for 1 hour. Volatile material was removed in vacuo and the residue was treated with 2M hydrochloric acid to pH1, followed by neutralisation with sodium carbonate solution and subsequent extraction with chloroform (3×100 cm³). The dried (MgSO₄) chloroform extract was evaporated to give an oil which was chromatographed on silica ("Merck" 60.9385) eluting with methanol:chloroform, 1:49, to give 2-[2-(1-benzyl-1,2,3,6-tetrahydropyrid-4-yl)ethyl]isothiazolidine-1,1-dioxide as an oil (4.5 g).

Preparation 7

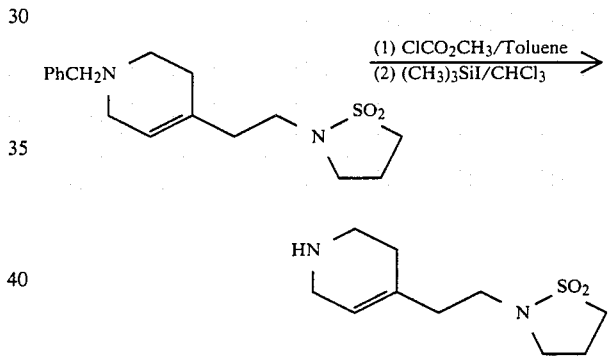

Methyl chloroformate (3.3 cm³) was added at room temperature to a stirred solution of 2-[2-(1-benzyl-1,2,3,6-tetrahydropyrid-4-yl)ethyl]isothiazolidine-1,1-dioxide (4.5 g) in toluene (20 cm³) and the mixture was heated under reflux for 16 hours. Volatile material was removed in vacuo to give the crude 2-[2-(1-methoxycarbonyl-1,2,3,6-tetrahydropyrid-4-yl)ethyl]isothiazolidine-1,1-dioxide as an oil (5.0 g).

A portion (4.6 g) of this material was taken without further purification into chloroform (10 cm³) and treated with iodotrimethylsilane (2.4 cm³) at room temperature, followed by warming at 50° C. for 2 hours. Methanol (20 cm³) was added, solvents were removed in vacuo and the residue was partitioned between chloroform (50 cm³) and 2M hydrochloric acid (100 cm³). The aqueous phase was basified to pH12 with 2M sodium hydroxide solution and the solution was extracted with chloroform (5×30 cm³). The dried (MgSO₄) extracts were evaporated to give 2-[2-(1,2,3,6-tetrahydropyrid-4-yl)ethyl]isothiazolidine-1,1-dioxide as an oil (2.0 g).

Preparation 8

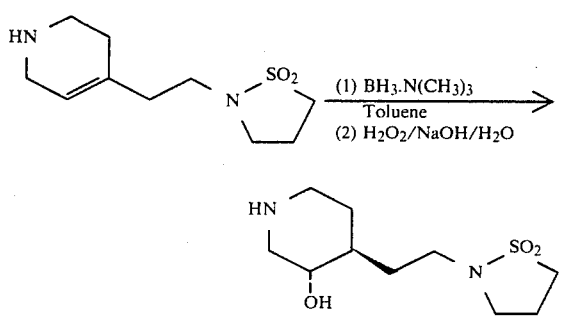

A stirred suspension of 2-[2-(1,2,3,6-tetrahydropyrid-4-yl)ethyl]isothiazolidine-1,1-dioxide (1.13 g) in toluene (10 cm³) was treated with Borane-Trimethylamine complex (0.52 g) and the mixture was heated under reflux for 24 hours. Volatile material was removed in vacuo, the residue was taken into THF (15 cm³) and treated with 5M sodium hydroxide (10 cm³) and 30% hydrogen peroxide (10 cm³). After 3 hours chloroform (50 cm³) was added and the aqueous phase was further extracted with chloroform (2×50 cm³). The combined organic extracts were dried (MgSO₄) and evaporated to give trans-2-[2-(3-hydroxypiperid-4-yl)ethyl]isothiazolidine-1,1-dioxide as an oil (0.35 g).

Preparations 9–14

The following intermediates were prepared similarly to Example 1, using 4-chloro-6,7-dimethoxyquinazoline, triethylamine and the appropriately substituted piperidine:

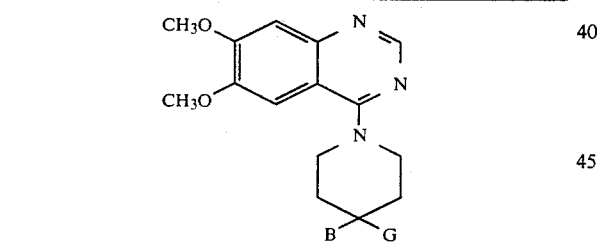

| Preparation No. | B | G | Form Isolated and m.p. (°C.) | Analysis % (Theoretical in brackets) | | |
|---|---|---|---|---|---|---|
| | | | | C | H | N |
| 9 | —H | CH₃<br>\|<br>—CHOH | Free base, 147.5–149° | 64.3<br>(64.3 | 7.4<br>7.3 | 13.0<br>13.2) |
| 10 | —H | Et<br>\|<br>—CHOH | Free base, 135° | 65.2<br>(65.0 | 7.6<br>7.6 | 12.7<br>12.5) |
| 11 | —OH | CH₃<br>\|<br>—CHCH₂OH | Free base, 173–175° | 62.0<br>(62.2 | 7.3<br>7.3 | 12.1<br>12.1) |
| 12 | —OH | —CH₂CH₂OH | Free base, 140° | 60.8<br>(61.2 | 6.9<br>6.9 | 12.8<br>12.6) |

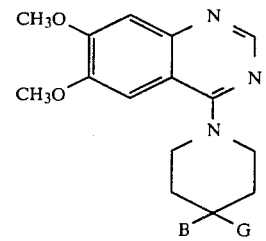

| Preparation No. | B | G | Form Isolated and m.p. (°C.) | Analysis % (Theoretical in brackets) | | |
|---|---|---|---|---|---|---|
| | | | | C | H | N |
| 13 | —H | OH<br>\|<br>—CHCH₂OH | Free base, 154–156° | 61.0<br>(61.2 | 6.9<br>6.9 | 12.4<br>12.6) |
| 14 | —H | OH<br>\|<br>—CCH₂OH<br>\|<br>CH₃ | Free base, 122–124° | 62.2<br>(62.2 | 7.3<br>7.3 | 12.1<br>12.1) |

Preparation 15

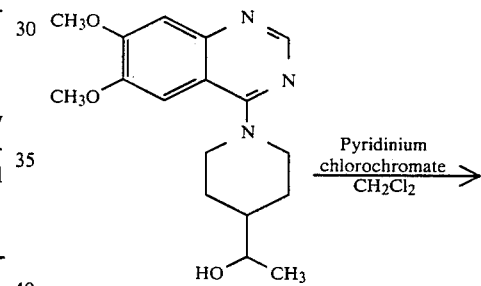

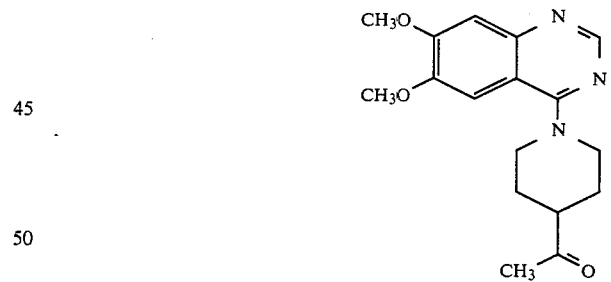

Pyridinium chlorochromate (6.2 g) was added at room temperature to a stirred solution of 6,7-dimethoxy-4-[4-(1-hydroxyethyl)piperid-1-yl]quinazoline (7.60 g) in dichloromethane (150 cm³) and the mixture was stirred for 24 hours. The mixture was filtered through "Avicel" (Trademark) and the solution was washed with 2M sodium hydroxide (3×50 cm³). The dried (MgSO₄) organic phase was evaporated and the residue chromatographed on silica ("Merck" 60.9385) eluting with chloroform to give a solid which was recrystallized from ethyl acetate to afford 6,7-dimethoxy-4-[4-(1-oxoethyl)piperid-1-yl]quinazoline, m.p. 116°–117° (3.05 g).

Analysis %: Found: C,64.7; H,6.6; N,13.4; Calculated for C₁₇H₂₁N₃O₃: C,64.7; H,6.7; N,13.3.

Preparation 16

The following compound was prepared similarly to Preparation 15, starting from 6,7-dimethoxy-4-[4-(1-hydroxypropyl)piperid-1-yl]quinazoline.

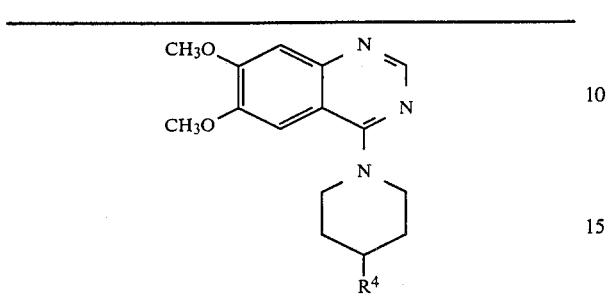

| Preparation No. | R$^4$ | Form Isolated and m.p. (°C.) | Analysis % (Theoretical in brackets) | | |
|---|---|---|---|---|---|
| | | | C | H | N |
| 16 | O<br>‖<br>—CCH$_2$CH$_3$ | Free base, 100° | 64.3<br>(65.6 | 6.8<br>7.0 | 12.5<br>12.8) |

Preparation 17

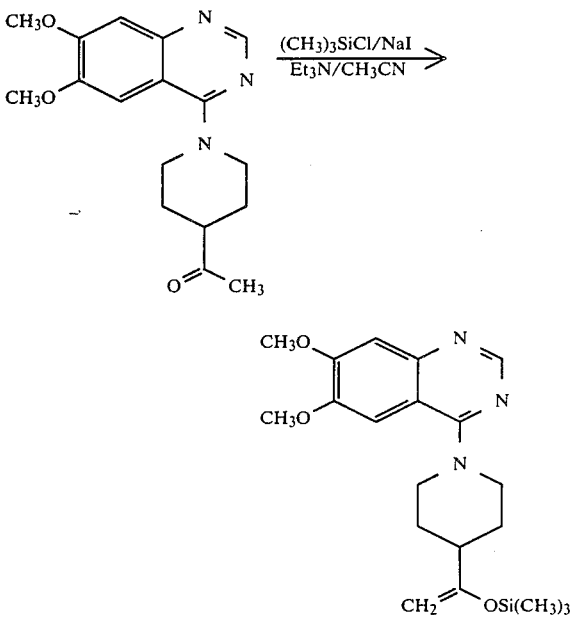

Triethylamine (2.25 cm$^3$) was added at 0° C. to a stirred solution of 6,7-dimethoxy-4-[4-(1-oxoethyl)piperid-1-yl]quinazoline (4.1 g) in acetonitrile (100 cm$^3$) followed by chlorotrimethyl-silane (2.0 cm$^3$) and sodium iodide (2.40 g). The mixture was heated under reflux for 4 hours, volatile material was removed in vacuo and the residue partitioned between chloroform (100 cm$^3$) and water (30 cm$^3$). The dried (MgSO$_4$) organic phase was evaporated and the residue was chromatographed on silica ("Merck" 60.9385) eluting with methanol:chloroform, 1:49, to give a solid (4.3 g), a small portion of which was triturated with ether to afford 6,7-dimethoxy-4-[4-(1-trimethylsilyloxy)ethenyl-piperid-1-yl]quinazoline, m.p. 122°–124°.

Analysis %: Found: C,62.0; H,7.6; N,10.8; Calculated for C$_{20}$H$_{29}$N$_3$O$_3$Si: C,62.0; H,7.5; N,10.8.

Preparation 18

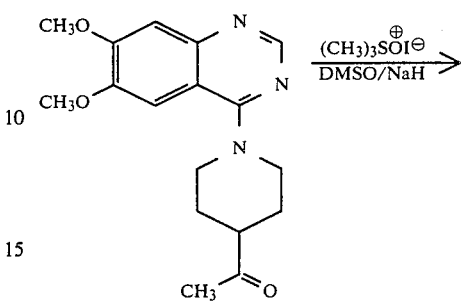

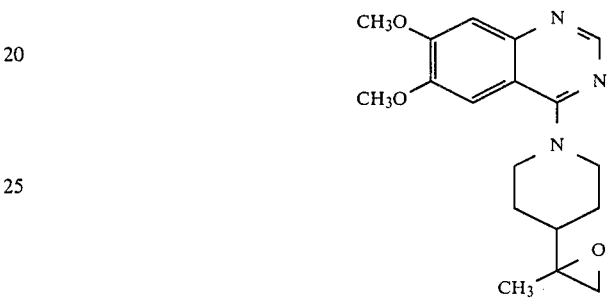

Trimethylsulphoxonium iodide (2.25 g) was added portionwise to a stirred suspension of sodium hydride (0.5 g of a 50% dispersion in oil) in dimethylsulphoxide (20 cm$^3$) and the mixture was stirred for 1 hour after which time 6,7-dimethoxy-4-[4-(1-oxoethyl)piperid-1-yl]quinazoline (3.15 g) was added in DMSO (10 cm$^3$). After 1 hour the mixture was poured into water (50 cm$^3$), extracted with dichloromethane (3×50 cm$^3$) and the dried extracts (MgSO$_4$) were evaporated to give an oil which was chromatographed on silica (Merck 60.9385) eluting with chloroform to give a viscous oil. Trituration with ether gave 2-methyl-2-[1-(6,7-dimethoxyquinazolin-4-yl)piperid-4-yl]oxirane slightly contaminated with the starting ketone (2.0 g).

Also prepared by a similar method from the appropriate ketone starting material was: 2-ethyl-2-[1-(6,7-dimethoxyquinazolin-4-yl)piperid-4-yl]oxirane, isolated as the hemihydrate, m.p. 138°–139°.

Analysis %: Found: C,65.2; H,7.1; N,11.9; C$_{19}$H$_{25}$N$_3$O$_3$.½H$_2$O requires: C,64.8; H,7.4; N,11.9.

Preparation 19

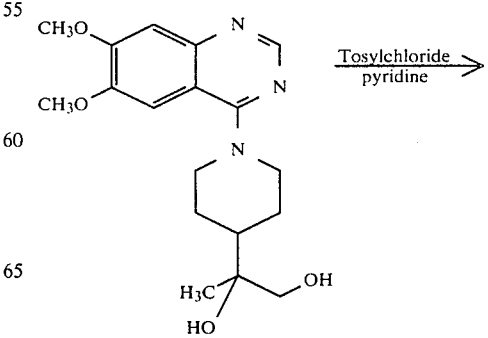

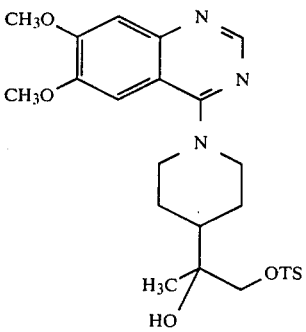

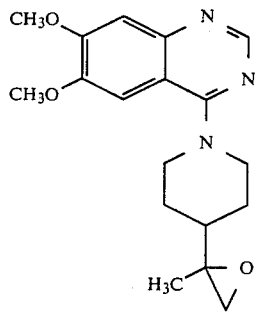

Toluene-4-sulphonylchloride (0.285 g) was added at 0° to a stirred solution of 2-[1-(6,7-dimethoxyquinazolin-4-yl)piperid-4-yl]propane-1,2-diol (0.35 g) in pyridine (3 cm³) and the mixture was stirred for 3 hours. The mixture was poured into a mixture of chloroform (20 cm³) and saturated sodium bicarbonate solution (20 cm³) and the dried (MgSO₄) chloroform layer was evaporated. The residue was chromatographed on silica ("Merck" 60.9385) eluting with methanol:chloroform, 1:49, to give an oil which was crystallised from ethyl acetate to afford 1-[4-toluenesulphonyloxy]-2-hydroxy-2-[1-(6,7-dimethoxyquinazolin-4-yl)piperid-4-yl]propane, m.p. 120°–124° (0.285 g).

Analysis %: Found: C,59.7; H,6.3; N,8.2; Calculated for C₂₅H₃₁N₃O₆S: C,59.9; H,6.2; N,8.4.

Also synthesised by a similar method from the appropriate starting materials were:

1-[4-toluenesulphonyloxy]-2-hydroxy-2-[1-(6,7-dimethoxyquinazolin-4-yl)piperid-4-yl]ethane, m.p. 135°–137°.

Found: C,59.4; H,6.1; N,8.6. C₂₄H₂₉N₃O₆S requires: C,59.1; H,6.0; N,8.6%;

1-(4-toluenesulphonyloxy)-2-[1-(6,7-dimethoxyquinazolin-4-yl)-4-hydroxypiperid-4-yl]ethane hemihydrate, m.p. 157°–160°.

Found: C,57.9; H,5.9; N,8.6. C₂₄H₂₉N₃O₆S.½H₂O requires: C,58.0; H,6.1; N,8.5%;

1-[4-toluenesulphonyloxy]-2-[1-(6,7-dimethoxyquinazolin-4-yl)-4-hydroxypiperid-4-yl]propane (free base, foam).

trans-1-[4-toluenesulphonyloxy]-b 2-[1-(6,7-dimethoxyquinazolin-4-yl)-3-t-butyldimethylsilyloxy-piperid-4-yl]propane (crude solids), diastereomers A and B.

Preparation 20

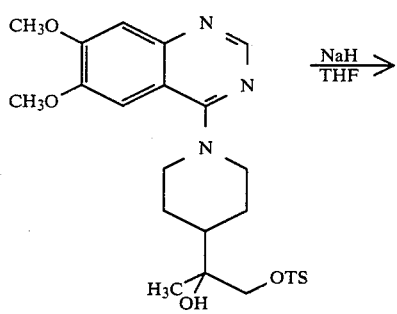

Sodium hydride (2.5 g of a 50% dispersion in oil) was added to a stirred suspension of 1-[4-toluenesulphonyloxy]-2-[1-(6,7-dimethoxyquinazolin-4-yl)piperid-4-yl]-2-hydroxypropane (8.6 g) in THF (20 cm³) and the mixture was heated under reflux for 16 hours. Volatile material was removed in vacuo, the residue was partitioned between chloroform (50 cm³) and water (50 cm³) and the aqueous phase was further extracted with chloroform (2×50 cm³). The combined, dried (MgSO₄) organic phase was evaporated and the residue was crystallised from ethyl acetate to afford 2-methyl-2-[1-(6,7-dimethoxy-quinazolin-4-yl)piperid-4-yl]oxirane, m.p. 125°–127.5° (5.0 g).

Analysis %: Found: C,65.0; H,7.0; N,12.6; Calculated for C₁₈H₂₃N₃O₃: C,65.6; H,7.0; N,12.8.

Also synthesized by a similar method from the appropriate tosyloxy starting material was:

2-[1-(6,7-dimethoxyquinazolin-4-yl)piperid-4-yl]oxirane (free base, oil).

Preparation 21

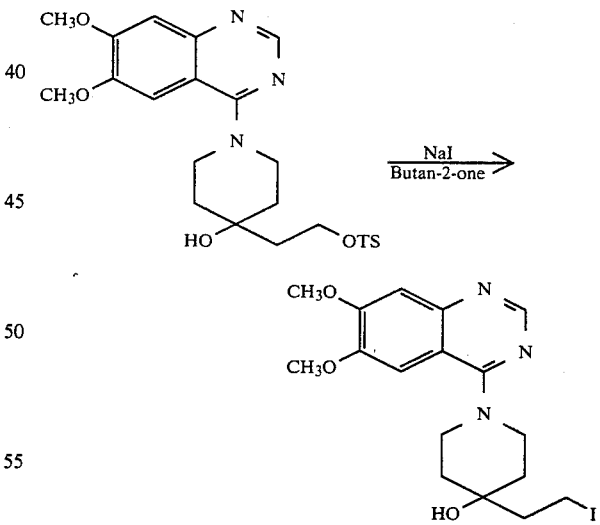

A mixture of 1-[4-toluenesulphonyloxy]-2-[1-(6,7-dimethoxyquinazolin-4-yl)-4-hydroxy-piperid-4-yl]ethane (0.6 g) and sodium iodide (1.84 g) in butan-2-one (10 cm³) was heated under reflux for 2.5 hours. Volatile material was removed in vacuo and the residue partitioned between chloroform (20 cm³) and water (20 cm³). The dried (MgSO₄) organic phase was evaporated and the residue was crystallized from ethyl acetate to afford 6,7-dimethoxy-4-[4-hydroxy-4-(2-iodoethyl)piperid-1-yl]quinazoline, m.p. 179°–181°, (0.3 g).

Analysis %: Found: C,46.2; H,5.0; N,9.4; Calculated for $C_{17}H_{22}N_3O_3I$: C,46.0; H,5.0; N,9.5.

Also synthesised by a similar method from the appropriate tosyloxy starting materials were:
6,7-dimethoxy-4-[4-hydroxy-4-(1-iodoprop-2-yl)piperid-1-yl]quinazoline (free base, solid); and
trans-6,7-dimethoxy-4-[3-t-butyldimethylsilyloxy-4-(1-iodoprop-2-yl)piperid-1-yl]quinazoline (crude solids), diastereomers A (m.p. 127°–129°) and B.

Preparation 22

The following intermediates were prepared similarly to Example 19 starting from the appropriate diastereomer of trans-1-(6,7-dimethoxyquinazolin-4-yl)-3-t-butyldimethylsilyloxy-4-(1-iodoprop-2-yl)piperidine and 2-sodioisothiazolidine-1,1-dioxide:
trans-2-{2-[1-(6,7-dimethoxyquinazolin-4-yl)-3-t-butyldimethylsilyloxypiperid-4-yl]prop-1-yl}isothiazolidine-1,1-dioxide (crude solid; diastereomer A); and
trans-2-{2-[1-(6,7-dimethoxyquinazolin-4-yl)-3-t-butyldimethylsilyloxypiperid-4-yl]prop-1-yl}isothiazolidine-1,1-dioxide (crude solid; diastereomer B).

Preparation 23

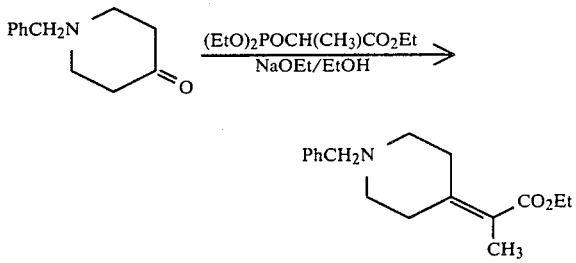

Triethyl-2-phosphonopropionate (71 g) was added at room temperature to a stirred solution of sodium ethoxide [prepared from sodium (5.98 g) and ethanol (500 cm³)] and after 10 minutes N-benzyl-4-piperidone (38.0 g) was added. After heating under reflux for 16 hours volatile material was removed in vacuo, water (100 cm³) and chloroform (200 cm³) were added and the organic phase was dried (MgSO₄) and evaporated. The resulting oil was distilled to give 1-benzyl-4-(1-ethoxycarbonyl-ethylidene)piperidine, b.p. 154°–156° 0.4 mm (46 g).

Preparation 24

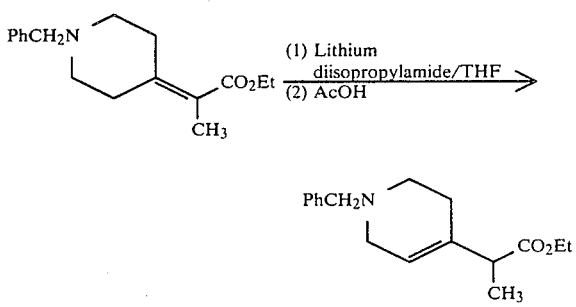

A solution of 1-benzyl-4-(1-ethoxycarbonylethylidine)piperidine (18.78 g) in THF (50 cm³) was added dropwise to a stirred solution of lithium diisopropylamide [made from n-BuLi (65 cm³ of a 1.6M solution in hexane) and diisopropylamine (14.4 cm³) in THF (50 cm³)] at −70° under nitrogen. After 10 minutes acetic acid (5.9 cm³) was added at −70° and after warming to room temperature, water (10 cm³) was added. Volatile material was removed in vacuo and the residue was partitioned between water (50 cm³) and chloroform (100 cm³). The dried (MgSO₄) organic layer was concentrated to give 1-benzyl-4-(1-ethoxycarbonyl)ethyl-1,2,3,6-tetrahydropyridine as an oil (18.0 g).

Preparation 25

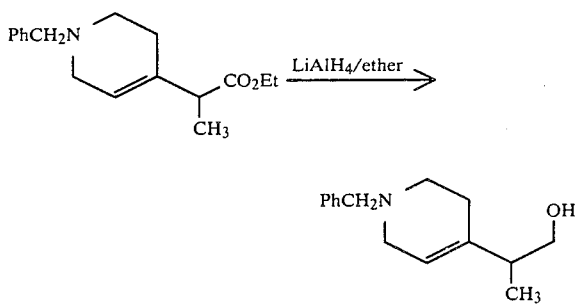

1-benzyl-4-(1-ethoxycarbonyl)ethyl-1,2,3,6-tetrahydropyridine (18.0 g) in dry ether (70 cm³) was added dropwise at 0° to a stirred suspension of lithium aluminium hydride (2.7 g) in ether (70 cm³) over 0.5 hours. After 1 hour 1M sodium hydroxide (15 cm³) solution was added dropwise over 0.5 hours and after stirring for a further 1 hour magnesium sulphate (10 g) was added. The mixture was filtered, the filtrate evaporated in vacuo and the residue distilled to afford 1-benzyl-4-(1-hydroxyprop-2-yl)-1,2,3,6-tetrahydropyridine as an oil b.p. 200° 0.05 mm (Kugelrohr) (12.43 g).

Also synthesized by a similar method from 1-benzyl-4-ethoxycarbonylmethyl-1,2,3,6-tetrahydropyridine was 1-benzyl-4-(2-hydroxyethyl)-1,2,3,6-tetrahydropiperidine, oil b.p 200° 0.05 mm (Kugelrohr).

Preparation 26

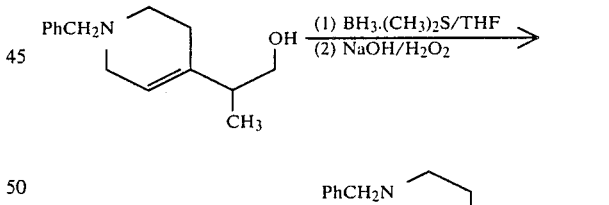

A solution of borane; dimethylsulphide complex (120 cm³ of a 2M solution in THF) was added at room temperature to a stirred solution of 1-benzyl-4-(1-hydroxyprop-2-yl)-1,2,3,6-tetrahydropyridine (18 g) in THF (300 cm³) under nitrogen. After warming at 50° for 4 hours the mixture was cooled to 0° and sodium hydroxide solution (160 cm³ of a 10% solution) was cautiously added dropwise over 0.5 hours. Hydrogen peroxide (150 cm³; 30 volume) was added slowly, the mixture was warmed at 60° for 4 hours and then volatile material was removed in vacuo. The residue was partitioned between water (100 cm³) and chloroform (250 cm³), and the organic extract was dried (MgSO₄) and evaporated to afford an oil. Chromatography on silica ("Merck" 60.9385) eluting with methanol:chloroform, 1:49, gave trans-1-benzyl-3-hydroxy-4-(1-hydroxyprop-2-yl)piperidine as a mixture of diastereomers (ca 2:1 by $^1$H-NMR) (15.5 g).

Also synthesized by a similar method from the appropriate starting material was:
trans-1-benzyl-3-hydroxy-4-(2-hydroxyethyl)piperidine, crude free base, oil.

Preparation 27

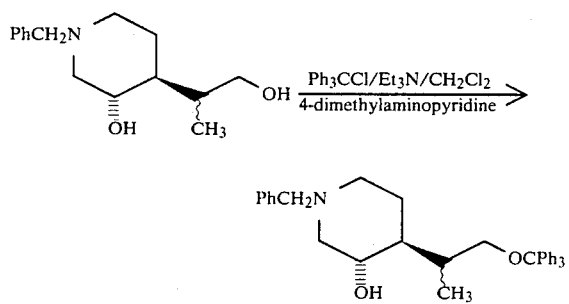

A mixture of trans-1-benzyl-hydroxy-4-(1-hydroxyprop-2-yl)piperidine (2:1 mixture of diastereomers) (15.0 g), triphenylmethylchloride (16.8 g), triethylamine (12.2 cm$^3$) and 4-dimethylamino-pyridine (0.35 g) was stirred in dichloromethane (120 cm$^3$) for 16 hours at room temperature. Water was then added and the organic phase was dried (MgSO$_4$) and evaporated to give an oil (24 g) which was chromatographed on silica ("Merck" 60.9385) eluting with ether to afford firstly ($R_F$ 0.50):
trans-1-benzyl-3-hydroxy-4-(1-triphenylmethoxy-prop-2-yl)piperidine, as a foam (7.0 g; diastereomer A) and secondly ($R_F$ 0.40)
trans-1-benzyl-3-hydroxy-4-(1-triphenyl-methoxyprop-2-yl)piperidine, as a foam (4.7 g; diastereomer B).

Also synthesized by a similar method from the appropriate starting material was:
trans-1-benzyl-3-hydroxy-4-(2-triphenylmethoxy-ethyl)piperidine, crude free base, foam.

Preparation 28

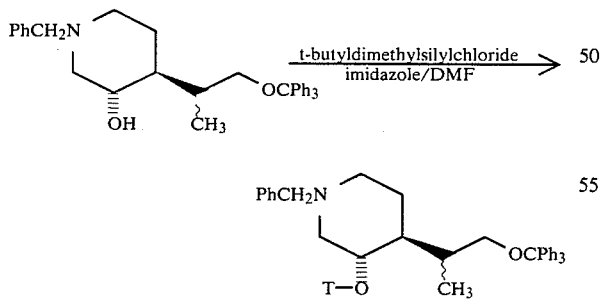

A mixture of trans-1-benzyl-3-hydroxy-4-(1-triphenylmethoxyprop-2-yl)piperidine (4.0 g; diastereomer A), t-butyldimethylsilylchloride (1.35 g) and imidazole (0.61 g) were stirred in DMF (15 cm$^3$) at 80° for 3 hours. Volatile material was removed in vacuo and the residue was partitioned between water (20 cm$^3$) and ethyl acetate (40 cm$^3$). The organic phase was dried (MgSO$_4$) and evaporated to give an oil which was chromatographed on silica ("Merck" 60.9385) eluting with ether to afford trans-1-benzyl-3-t-butyldimethylsilyloxy-4-(1-triphenylmethoxyprop-2-yl)piperidine as a foam (4.5 g; diastereomer A).

Also synthesized by a similar method from appropriate starting materials were:
trans-1-benzyl-3-t-butyldimethylsilyloxy-4-(1-triphenylmethoxyprop-2-yl)piperidine, crude oil (diastereomer B); and
trans-1-benzyl-3-t-butyldimethylsilyloxy-4-(2-triphenylmethoxyethyl)piperidine, crude oil.

Preparation 29

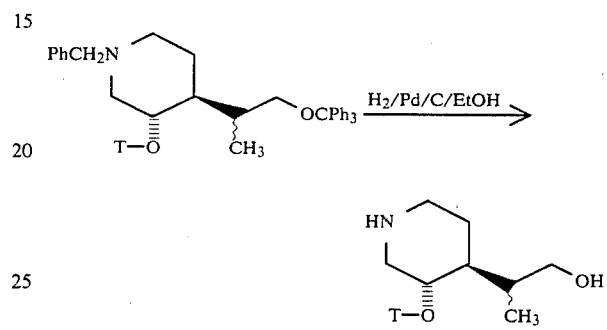

Trans-1-benzyl-3-t-butyldimethylsilyloxy-4-(1-triphenylmethoxyprop-2-yl)piperidine (4.5 g; diastereomer A) was hydrogenated in ethanol (60 cm$^3$) at 60° and 60 p.s.i. pressure over 10% palladium on carbon (0.9 g) for 5 hours. The solution was cooled, filtered through "Avicel" to remove the catalyst and evaporated in vacuo to afford trans-3-t-butyldimethylsilyloxy-4-(1-hydroxyprop-2-yl)piperidine as a crude oil (diastereomer A).

Also synthesised by a similar method from appropriate starting materials were:
Trans-3-t-butyldimethylsilyloxy-4-(1-hydroxyprop-2-yl)piperidine, crude oil (diastereomer B); and
trans-3-t-butyldimethylsilyloxy-4-(2-hydroxyethyl)-piperidine, crude oil.

Preparations 30–32

The following intermediates were prepared similarly to Example 1, using 4-chloro-6,7-dimethoxy-quinazoline, triethylamine and the appropriately substituted piperidine:

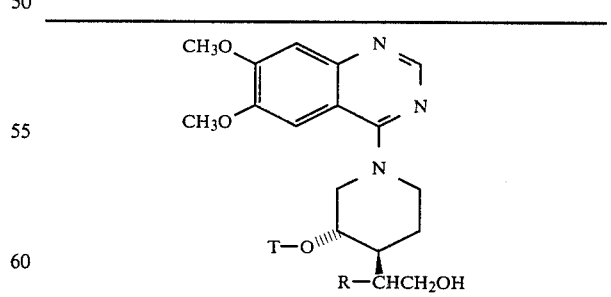

| Preparation No. | R | Form Isolated and m.p. (°C.) | Analysis % (Theoretical in brackets) | | |
|---|---|---|---|---|---|
| | | | C | H | N |
| 30 | H | Free base, 131–133° | 61.6 (61.7) | 8.3 (8.3) | 9.6 (9.4) |
| 31 | | Free base, | 62.2 | 8.5 | 9.1 |

43

-continued

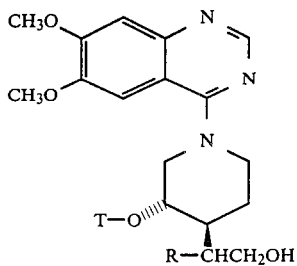

R—CHCH2OH

| Preparation No. | R | Form Isolated and m.p. (°C.) | Analysis % (Theoretical in brackets) | | |
|---|---|---|---|---|---|
| | | | C | H | N |
| 32 (diastereomer A) (diastereomer B) | CH3 | 156–157° Crude free base, foam | (62.4 | 8.5 | 9.1) |

Preparation 33

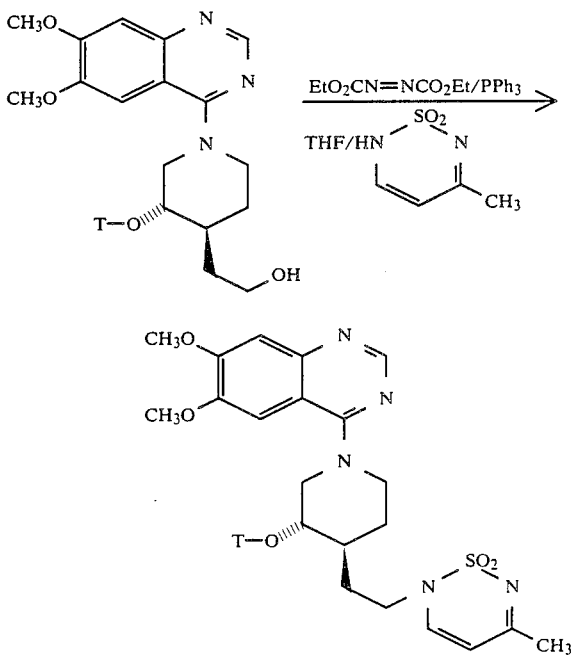

Diethylazodicarboxylate (0.28 cm³) was added to a stirred solution of trans-1-(6,7-dimethoxyquinazolin-4-yl)-3-t-butyldimethylsilyloxy-4-(2-hydroxyethyl)piperidine (0.67 g), triphenyl phosphine (0.47 g) and 2H-5-methyl-1,2,6-thiadiazine-1,1-dioxide (0.26 g) in THF (5 cm³). After heating under reflux for 1 hour volatile material was removed in vacuo and the residue was chromatographed on silica ("Merck" 60.9385) eluting with methanol:ethyl acetate, 1:19, to afford trans-2-{-[1-(6,7-dimethoxyquinazolin-4-yl)-3-t-butyldimethylsilyloxypiperid-4-yl]ethyl}-5-methyl-1,2,6-thiadiazine-1,1-dioxide as a foam (0.80 g).

Also synthesised by a similar method from the appropriate starting materials were:
trans-2-{2-[1-(6,7-dimethoxyquinazolin-4-yl)-3-t-butyl-dimethylsilyloxypiperid-4-yl]prop-1-yl}-5-methyl-1,2,6-thiadiazine-1,1-dioxide (foams) diastereomers A and B.

Preparation 34

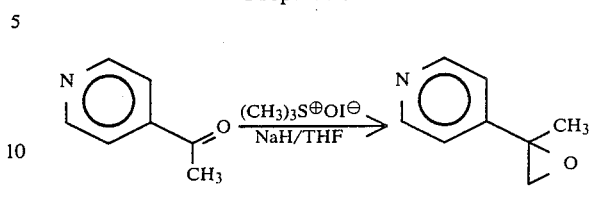

Sodium hydride (5.0 g of a 50% dispersion in oil) was added portionwise to a stirred suspension of trimethyl-sulphoxonium iodide (22.0 g) in THF (150 cm³) and the mixture was heated under reflux for 3 hours. After cooling to 40°, 4-acetyl-pyridine (10.0 g) was added and the mixture was again heated under reflux for 1 hour. The cooled mixture was evaporated in vacuo, partitioned between ether (100 cm³) and water (50 cm³) and the aqueous phase was further extracted with ether (2×50 cm³). The combined dried extracts were evaporated to afford 2-methyl-2-[4-pyridyl]oxirane as a crude oil.

Preparation 35

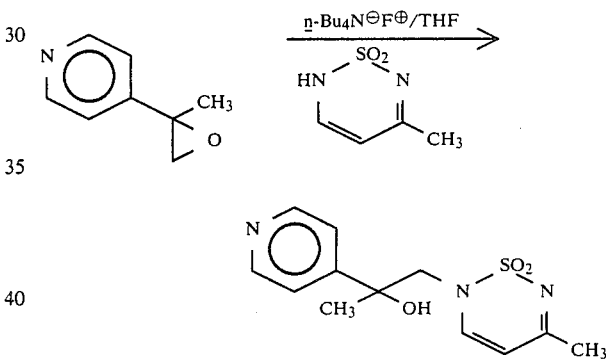

A mixture of 2-methyl-2-[4-pyridyl]oxirane (13.72 g), 2H-5-methyl-1,2,6-thiadiazine-1,1-dioxide (17.8 g) and tetrabutylammonium fluoride (12.2 cm³; 1M solution in THF) was heated at 50° with stirring under nitrogen for 48 hours. Volatile material was removed in vacuo and the residue chromatographed on silica ("Merck" 60.9385), eluting with chloroform to afford an oil which crystallised on trituration with ethyl acetate to yield 2-[2-(4-pyridyl)-2-hydroxy]prop-1-yl-5-methyl-2H-1,2,6-thiadiazine-1,1-dioxide as microcrystals, m.p. 167°–169° (5.21 g).

Analysis %: Found: C,51.1; H,5.4; N,14.9; Calculated for C12H15N3O3S: C,51.2; H,5.4; N,14.9.

Preparation 36

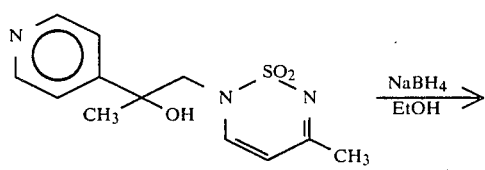

-continued

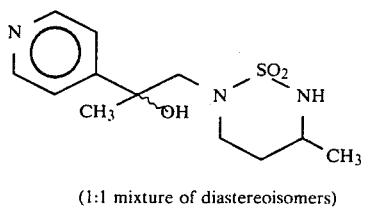

(1:1 mixture of diastereoisomers)

A stirred suspension of 2-[2-(4-pyridyl)-2-hydroxy]-prop-1-yl-5-methyl-2H-1,2,6-thiadiazine-1,1-dioxide (3.59 g) in ethanol (50 cm³) was treated with sodium borohydride (0.5 g). After 1 hour 2M hydrochloric acid (20 cm³) was added, volatile material was removed in vacuo and the residue was partitioned between aqueous sodium carbonate solution and chloroform. The aqueous phase was further extracted with chloroform (3×100 cm³) and the combined dried extracts were evaporated in vacuo to yield an oil which was triturated with ethyl acetate to afford a solid which was recrystallised from ethyl acetate to give 2-[2-(4-pyridyl)-2-hydroxy]prop-1-yl-5-methyltetrahydrothiadiazine-1,1-dioxide, m.p. 188°–191° [1.057 g; diastereomer A, $R_F$ 0.60 (2 elutions); cyclohexane:dioxan, 1:2]. The mother liquors were chromatographed on silica ("Merck" 60.9385) eluting with cyclohexane:dioxan, 1:2, to give an oil which crystallised from ethyl acetate to afford 2-[2-(4-pyridyl)-2-hydroxy]prop-1-yl-5-methyl-tetrahydrothiadiazine-1,1-dioxide, m.p. 170.5°–172.5° [1.295 g; diastereomer B, $R_F$ 0.65 (2 elutions); cyclohexane:dioxan, 1.2]. Chromatography and crystallisation of the mother liquors yielded further pure samples of both isomers giving total yields of firstly:

diastereomer A, 1.476 g.

Analysis %: Found: C,50.7; H,6.6; N,14.7; Calculated for $C_{12}H_{19}N_3O_3S$: C,50.5; H,6.7; N,14.7;
and secondly:

diasteroemer B, 1.463 g.

Analysis %: Found: C,50.5; H,7.1; N,14.6; Calculated for $C_{12}H_{19}N_3O_3S$: C,50.5; H,6.7; N,14.7.

Preparation 37

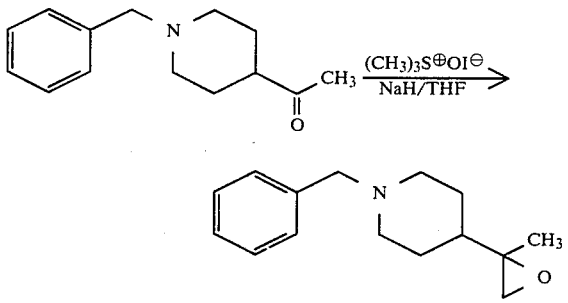

A suspension of trimethylsulphoxonium iodide (44 g) in THF (193 cm³) was treated with sodium hydride (10.1 g of a 57% dispersion in oil) and heated under reflux for 3.5 hours under nitrogen. The mixture was cooled to room temperature and stirred as 4-acetyl-1-benzylpiperidine (45.4 g; prepared as described by A. T. Nielsen et. al., J. Org. Chem., 29, 2898–2903, 1964) was added over 15 minutes. The mixture was heated under reflux for 1 hour, cooled, and treated with ethanol (3 cm³) and then water (60 cm³). The THF was distilled off and the resulting concentrate was extracted with ethyl acetate (3×60 ml). The dried (MgSO₄) organic extracts were filtered and evaporated to give the crude product as an oil (51.9 g; 98.6% yield corrected for presence of oil from sodium hydride) of 93.4% purity (GLC normalisation assay).

A 5 g sample of the crude product was dissolved in diethyl ether (50 cm³), clarified by filtration through "Avicel" and treated with a solution of maleic acid (2.51 g) in methanol (12.5 cm³). Stirring for 45 minutes at 5° C., followed by filtration and recrystallisation from isopropanol (13 cm³) gave 2-methyl-2-[4-(1-benzyl)-piperidyl]oxirane maleate (3.39 g) as white crystals, m.p. 141°–145° C.

Analysis %: Found: C,65.7; H,7.3; N,4.1; Calculated for $C_{19}H_{25}NO_5$: C,65.7; H,7.25; N,4.0.

Preparation 38

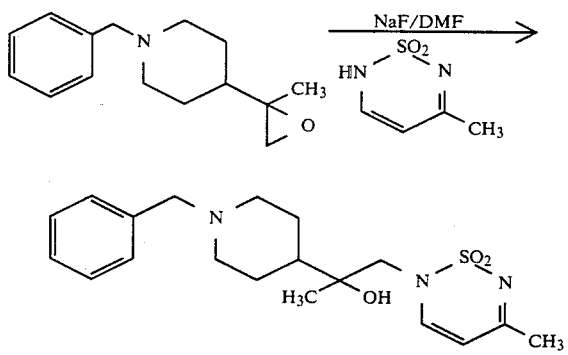

A mixture of 2-methyl-2-[4-(1-benzyl)-piperidyl]oxirane (158.4 g), 5-methyl-2H-1,2,6-thiadiazine-1,1-dioxide (100 g), and anhydrous sodium fluoride (19.9 g) in DMF (555 cm³) was heated at 105° C. for 7 hours. The mixture was evaporated, the residue dissolved in chloroform (1.6 l), and the solution clarified by filtration through "Avicel" (Trademark). The chloroform solution was run onto a column of Merck 70–230 mesh Kieselgel 60 (1.5 kg) and the column was eluted with chloroform:methanol, 19:1. Combination and evaporation in vacuo of the requisite fractions gave the crude product (90.9 g), which was crystallised from ethyl acetate (230 cm³) to afford 2-[2-{4-(1-benzyl)piperidyl}-2-hydroxy]prop-1-yl-5-methyl-2H-1,2,6-thiadiazine-1,1-dioxide (59.7 g; 23.1%) as buff crystals, m.p. 149°–151° C.

Analysis %: Found: C,60.7; H,7.3; N,10.9; S,8.4; Calculated for $C_{19}H_{27}N_3O_3S$: C,60.5; H,7.2; N,11.1; S,8.5.

Preparation 39

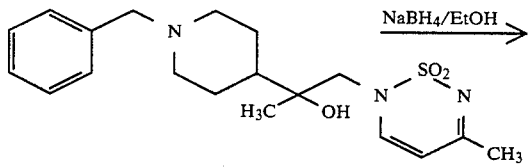

47
-continued

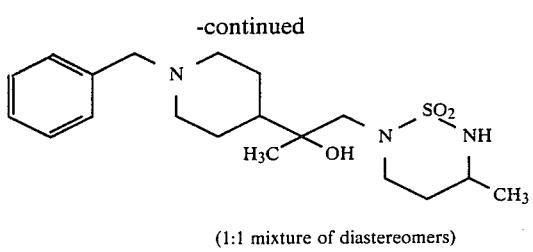

(1:1 mixture of diastereomers)

(A) A suspension of 2-[2-{4-(1-benzyl)piperidyl}-2-hydroxy]prop-1-yl-5-methyl-2H-1,2,6-thiadiazine-1,1-dioxide (163 g) in ethanol (535 cm$^3$) was treated with sodium borohydride (11.9 g). After heating under reflux for 2 hours the cooled solution was acidified to pH0.2 with dilute hydrochloric acid and evaporated to dryness. The residue was stirred with saturated aqueous sodium bicarbonate solution (1.5 l) and chloroform (1.5 l) and the layers separated. The aqueous layer was further extracted with chloroform (0.75 l and 0.25 l) and the combined, dried chloroform extracts were evaporated to give 2-[2-{4-(1-benzyl)piperidyl}-2-hydroxy]-prop-1-yl-5-methyl-tetrahydro-1,2,6-thiadiazine-1,1-dioxide (165.6 g; 100%) as a glassy solid which was a 50:50 mixture of two diastereomers by proton N.M.R.

(B) To a solution of the above mixture (165 g) in isopropanol (660 cm$^3$) was added a 5.6N solution of hydrogen chloride in isopropanol (85 cm$^3$). The solution was kept overnight in the refrigerator and the filtered solid was recrystallised from ethanol (500 cm$^3$) and granulated for 4 hours at 5° C. Filtration gave 2-[2-{4-(1-benzyl)piperidyl}-2-hydroxy]prop-1-yl-5-methyl-tetrahydro-1,2,6-thiadiazine-1,1-dioxide monohydrochloride, diastereomer A (55.5 g; 30.7%) as white crystals, m.p. 239°-140° C.

Analysis %: Found: C,54.2; H,7.7; N,9.9; Calculated for C$_{19}$H$_{32}$ClN$_3$O$_3$S: C,54.6; H,7.7; N, 9.9.

Preparation 40

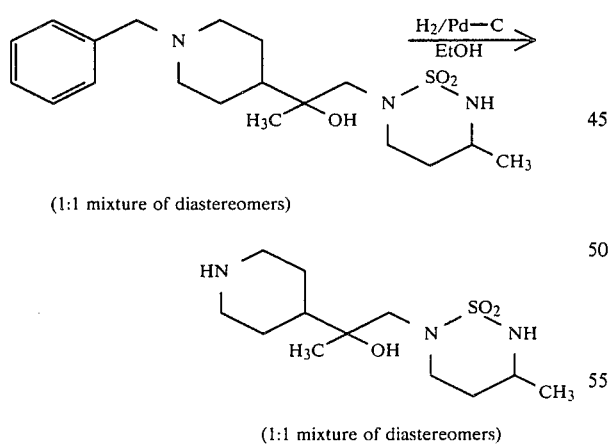

(1:1 mixture of diastereomers)

A solution of 2-[2-{4-(1-benzyl)piperidyl}-2-hydroxy]prop-1-yl-5-methyltetrahydro-1,2,6-thiadiazine-1,1-dioxide (41.1 g) in ethanol (400 cm$^3$) was treated with 5% palladised charcoal (12 g of 50% water wet catalyst) and hydrogenated at 50° C. and 50 p.s.i. for 6 hours. Filtration and evaporation gave the crude product as a solid (30.4 g; 99.3% as a 1:1 mixture of two diastereomers. A sample of this material (6.26 g) was recrystallised from deionised water (13.5 cm$^3$) to give a solid which was filtered and washed with water (4 cm$^3$)

48 to afford 2-[2-(4-piperidyl)-2-hydroxy]prop-1-yl-5-methyltetrahydro-1,2,6-thiadiazine-1,1-dioxide, diastereomer A (1.40 g; 22.4%) as white crystals, m.p. 189°-196° C.

We claim:

1. A piperidinoquinazoline compound of the formula

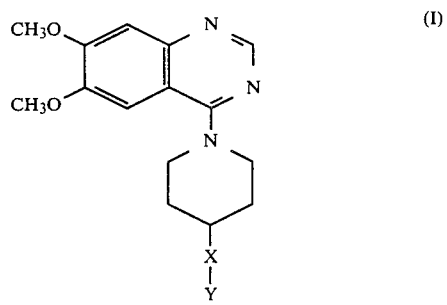 (I)

or a pharmaceutically acceptable salt thereof, wherein:
X is an alkylene group of the formula

—CHCH$_2$—, where R is H, CH$_3$ or C$_2$H$_5$;
Y is a group of the formula:

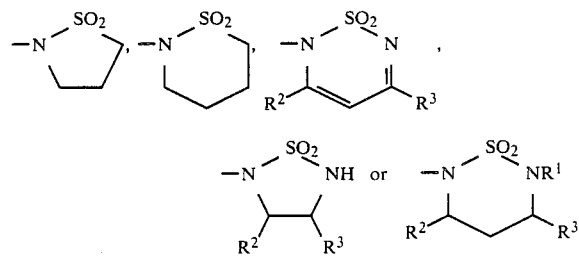

where R$^1$ is H or C$_1$–C$_4$ alkyl, and R$^2$ and R$^3$ are each independently H or CH$_3$; and either:
(i) the piperidine ring is further substituted with a hydroxy group in the 3- or 4-position, and, if it is substituted with a hydroxy group in the 3-position, it can be further substituted in the same position with a C$_1$–C$_4$ alkyl group; or
(ii) the carbon atom of X attached to the piperidine ring is further substituted with a hydroxy group.

2. A compound according to claim 1 of the formula

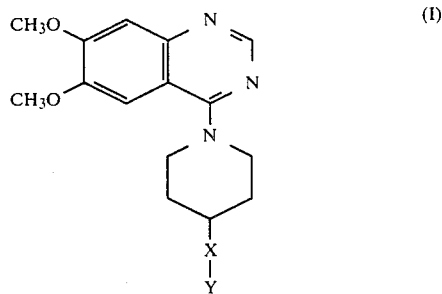 (I)

or a pharmaceutically acceptable salt thereof, wherein:
X is an alkylene group of the formula $$-\overset{R}{\underset{|}{C}}HCH_2-,$$

where R is H, CH₃ or C₂H₅;
Y is a group of the formula:

[structures: -N(SO₂)(CH₂CH₂), -N(SO₂)(CH₂CH₂CH₂), -N(SO₂)N=C(R²)-CH=C(R³)-, -N(SO₂)NH with R²,R³, -N(SO₂)NR¹ with R²,R³]

where R¹ is H or C₁–C₄ alkyl, and R² and R³ are each independently H or CH₃;
and the piperidine ring is further substituted with a hydroxy group in the 3- or 4-position, and, if it is substituted with a hydroxy group in the 3-position, it can be further substituted in the same position with a C₁–C₄ alkyl group.

3. A compound according to claim 2 of the formula

[structure with 6,7-dimethoxyquinazoline attached to piperidine bearing A, B, X-Y substituents]

or a pharmaceutically acceptable salt thereof, wherein X and Y are as defined in claim 2;
and A and B each hydrogen or hydroxy, provided that A and B are always different.

4. A compound according to claim 3, wherein Y is

[three structures]

5. A compound according to claim 4, wherein A is hydroxy and B is hydrogen.

6. A compound according to claim 5, wherein X is —CH(CH₃)—CH₂—.

7. A compound according to claim 1 of the formula

[structure (I): 6,7-dimethoxyquinazolin-4-yl linked to 4-substituted piperidine with X-Y]

(I)

or a pharmaceutically acceptable salt thereof, wherein:
X is a group of the formula $$-\overset{R}{\underset{\underset{OH}{|}}{C}}-CH_2-,$$

where R is H, CH₃ or C₂H₅; and
Y is a group of the formula:

[structures]

where R¹ is H or C₁–C₄ alkyl, and R² and R³ are each independently H or CH₃.

8. A compound according to claim 7, wherein Y is

[three structures including CH₃ substituents]

9. A compound according to claim 8, wherein X is $$-\overset{R}{\underset{\underset{OH}{|}}{C}}-CH_2-$$

wherein R is CH₃ or C₂H₅.

10. A compound according to claim 9, wherein R is methyl and Y is

[pyrrolidine sulfonyl structure]

11. A compound according to claim 9, wherein R is methyl and Y is

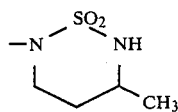

12. A method of stimulating the heart of a mammalian subject, which comprises administering to a mammalian subject in need of such treatment an effective heart stimulating amount of a piperidinoquinazoline compound of the formula

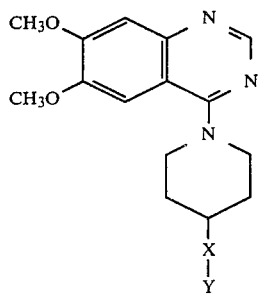

or a pharmaceutically acceptable salt thereof, wherein:
X is an alkylene group of the formula

where R is H, $CH_3$ or $C_2H_5$;
Y is a group of the formula:

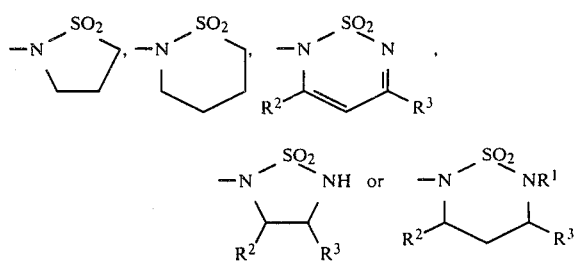

where $R^1$ is H or $C_1$-$C_4$ alkyl, and $R^2$ and $R^3$ are each independently H or $CH_3$; and either:
(i) the piperidine ring is further substituted with a hydroxy group in the 3- or 4-position, and, if it is substituted with a hydroxy group in the 3-position, it can be further substituted in the same position with a $C_1$-CHD 4 alkyl group; or
(ii) the carbon atom of X attached to the piperidine ring is further substituted with a hydroxy group.

13. The method according to claim 12, wheren X is

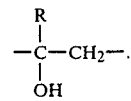

14. The method according to claim 13, wherein R is $CH_3$ or $C_2H_5$ and Y is

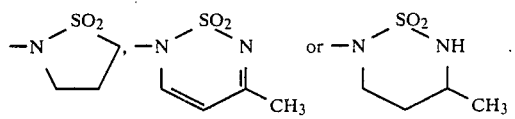

15. The method according to claim 14, wherein R is methyl and Y is

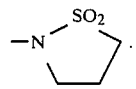

16. The method according to claim 14, wherein R is methyl and Y is

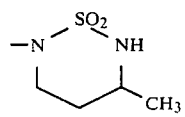

17. A mammalian heart stimulating pharmaceutical composition which comprises a piperidinoquinazoline compound according to claim 1 and a pharmaceutically acceptable carrier, and wherein the weight ratio of said piperidinoquinazoline compound to said carrier is in the range from 4:1 to 1:40.

* * * * *